US008538706B2

(12) United States Patent
Desmet et al.

(10) Patent No.: US 8,538,706 B2
(45) Date of Patent: Sep. 17, 2013

(54) METHOD FOR AFFINITY SCORING OF PEPTIDE/PROTEIN COMPLEXES

(75) Inventors: Johan Desmet, Kortrijk (BE); Geert Meersseman, Brussels (BE); Nathalie Boutonnet, Rhode St. Genese (BE); Jurgen Pletinckx, Deinze (BE); Krista De Clercq, Bavikhove (BE); Ignace Lasters, Antwerp (BE)

(73) Assignee: Lonza Biologics PLC, Slough (GB)

( * ) Notice: Subject to any disclaimer, the term of this patent is extended or adjusted under 35 U.S.C. 154(b) by 0 days.

(21) Appl. No.: 13/270,931

(22) Filed: Oct. 11, 2011

(65) Prior Publication Data
US 2012/0278054 A1 Nov. 1, 2012

Related U.S. Application Data

(62) Division of application No. 11/568,108, filed as application No. PCT/BE2005/000052 on Apr. 21, 2005, now abandoned.

(30) Foreign Application Priority Data

Apr. 21, 2004 (EP) ..................................... 04447103

(51) Int. Cl.
*G06F 19/16* (2011.01)
*G06F 19/18* (2011.01)
(52) U.S. Cl.
USPC .............................................. 702/19; 703/11
(58) Field of Classification Search
None
See application file for complete search history.

(56) References Cited

U.S. PATENT DOCUMENTS
2005/0089878 A1 4/2005 Debe et al.

FOREIGN PATENT DOCUMENTS
WO   WO 99/45954       9/1999
WO   WO 03/105058 A2   12/2003

OTHER PUBLICATIONS

Archontis, G. et al., "Binding Free Energies and Free Energy Components from Molecular Dynamics and Poisson-Boltzmann Calculations. Application to Amino Acid Recognition by Aspartyl-tRNA Synthetase," *J. Mol. Biol.*, vol. 306, pp. 307-327 (2001).
Desmet, J. et al., "Anchor Profiles of HLA-Specific Peptides: Analysis by a Novel Affinity Scoring Method and Experimental Validation," *Proteins*, vol. 58, pp. 53-69 (2005).
Michielin, O. et al., "Binding Free Energy Differences in a TCR-Peptide-MHC Complex Induced by a Peptide Mutation: A Simulation Analysis," *J. Mol. Biol.*, vol. 324, pp. 547-569 (2002).
Searle et al., "Partitioning of free energy contributions in the estimation of binding contstants: Residual motions and consequences for amide-amide hydrogen bond strengths," *J. Am. Chem. Sot.* (1992) 114: 10697-10704.
Moon et al., "Computer design of bioactive molecules: A method for receptor-based de Novo ligand design," *Proteins: Structure, Function, and Bioinformatics* (2004) 11 (4): 314-328.
Shapira et al., "Prediction of the binding energy for small molecules, peptides, and proteins," *J. Mol. Recognit.*(1999) 12: 177-190.
Zhang et al., "Solven models for protein-ligand binding: Comparison of implicit solvent poisson and surface generalized born models with explicit solvent simulations," *Journal of Computational Chemistry* (2001) 22 (6): 591-607.
Levy et al., "Computer simulations with explicit solvent: recent progress in the thermodynamic decomposition of free energies and in modeling electrostatic effects," *Annu Rev Phys Chem.* PubMed ID: 9933909 (1998) 49: 531-67.
Batalia et al., "Peptide Binding by Class I and Class II MHC Molecules." *Biopolymers*, 1997, pp. 281-302.
Berman et al., "The Protein Data Bank." *Nucleic Acids Research*, vol. 28, No. 1, 2000, pp. 235-242.
Bjorkman et al., "The Foreign Antigen Binding Site and T Cell Recognition Regions of Class I Histocompatibility Antigens." *Nature*, vol. 329, Oct. 1987, pp. 512-518.
Böhm, "The Development of a Simple Empirical Scoring Function to Estimate the Binding Constant for a Protein-Ligand Complex of Known Three-Dimensional Structure." *J. Comp.-Aided Mol. Des.*, vol. 8, 1994, pp. 243-256.
Brooks et al., "CHARMM: A Program for Macromolecular Energy, Minimization, and Dynamics Calculations." *J. Comput. Chem.*, vol. 4, No. 2, 1983, pp. 187-217.
Chen et al., "Naturally Processed Peptides Longer than Nine Amino Acid Residues Bind to the Class I MHC Molecule HLA-A2.1 with High Affinity and in Different Conformations." *J. Immunol.*, vol. 152, 1994, p. 2874-2881.
De Maeyer et al., "All in One: A Highly Detailed Rotamer Library Improves Both Accuracy and Speed in the Modelling of Sidechains by Dead-End Elimination." *Folding & Design*, vol. 2, Jan. 1997, pp. 53-66.
Desmet et al., "Flexible Docking of Peptide Ligands to Proteins." *Methods in Molecular Biology*, vol. 143, 2000, pp. 359-376.
Desmet et al., "Computation of the Binding of Fully Flexible Peptides to Proteins with Flexible Side Chains." *FASEB J.*, vol. 11, Feb. 1997, pp. 164-172.

(Continued)

*Primary Examiner* — Michael Borin
(74) *Attorney, Agent, or Firm* — Merchant & Gould P.C.

(57) ABSTRACT

The present invention is related to a quantitative structure-based affinity scoring method for peptide/protein complexes. More specifically, the present invention comprises a method that operates on the basis of a highly specific force field function (e.g. CHARMM) that is applied to all-atom structural representations of peptide/receptor complexes. Peptide side-chain contributions to total affinity are scored after detailed rotameric sampling followed by controlled energy refinement. The method of the invention further comprises a de novo approach to estimate dehydration energies from the simulation of individual amino acids in a solvent box filled with explicit water molecules and applying the same force field function as used to evaluate peptide/receptor complex interactions.

20 Claims, 2 Drawing Sheets

(56) References Cited

OTHER PUBLICATIONS

Figure 1:
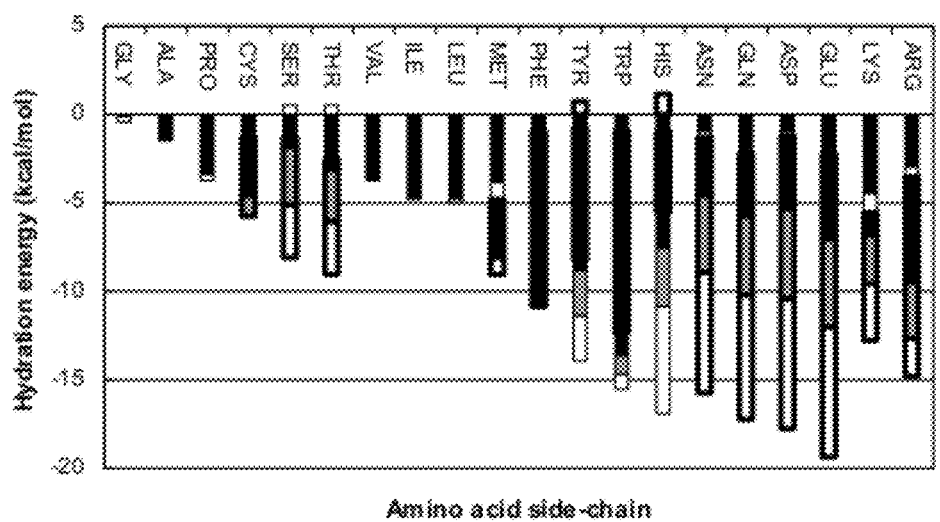

Desmet et al., "Fast and Accurate Side-Chain Topology and Energy Refinement (FASTER) as a New Method for Protein Structure Optimization." *Proteins: Structure, Function, and Genetics*, vol. 48, 2002, pp. 31-43.
Doytchinova et al, "Physicochemical Explanation of Peptide Binding to HLA-A 0201 Major Histocompatibility Complex: A Three-Dimensional Quantitative Structure-Activity Relationship Study." *Proteins: Structure, Function, and Genetics*, vol. 48, 2002, pp. 505-518.
Doytchinova et al., "Additive Method for the Prediction of Protein-Peptide Binding Affinity. Application to the MHC Class I Molecule HLA-A 0201." *J. Proteome Research*, vol. 1, 2002, pp. 263-272.
Dunbrack, Jr. et al., "Conformational Analysis of the Backbone-Dependent Rotamer Preferences of Protein Sidechains." *Structural Biology*, vol. 1, No. 5, May 1994, pp. 334-340.
Eisenberg et al., "Solvation Energy in Protein Folding and Binding." *Nature*, vol. 319, Jan. 1986, pp. 199-203.
Engelhard, "Structure of Peptides Associated with MHC Class I Molecules." *Current Opinion in Immunology*, vol. 6, 1994, pp. 13-23.
Falk et al., "Allele-Specific Motifs Revealed by Sequencing of Self-Peptides Eluted from MHC Molecules." *Nature*, vol. 351, May 1991, pp. 290-296.
Froloff et al., "On the Calculation of Binding Free Energies Using Continuum Methods: Application to MHC Class I Protein-Peptide Interactions." *Protein Science*, vol. 6, 1997, pp. 1293-1301.
Gilis et al., "Stability Changes Upon Mutation of Solvent-Accessible Residues in Proteins Evaluated by Database Derived Potentials." *J. Mol. Biol.*, vol. 257, 1996, pp. 1112-1126.
Gordon et al., "Energy Functions for Protein Design." *Current Opinion in Structural Biology*, vol. 9, 1999, pp. 509-513.
Guerois et al., "Predicting Changes in the Stability of Proteins and Protein Complexes: A Study of More Than 1000 Mutations." *J. Mol. Biol.*, vol. 320, 2002, pp. 369-387.
Guo et al., "Different Length Peptides Bind to HLA-Aw68 Similarly at Their Ends but Bulge Out in the Middle." *Nature*, vol. 360, Nov. 1992, pp. 364-366.
Jernigan et al., "Structure-Derived Potentials and Protein Simulations." *Current Opinion in Structural Biology*, vol. 6, 1996, pp. 195-209.
Jorgensen et al., "Comparison of Simple Potential Functions for Simulating Liquid Water." *J. Chem. Phys.*, vol. 79, No. 2, Jul. 1983, pp. 926-935.
Kessler et al., "Competition-Based Cellular Peptide Binding Assays for 13 Prevalent HLA Class I Alleles Using Fluorescein-Labeled Synthetic Peptides." *Human Immunology*, vol. 64, 2003, pp. 245-255.
Lazaridis et al., "Effective Energy Function for Proteins in Solution." *Proteins: Structure, Function, and Genetics*, vol. 35, 1999, pp. 133-152.
Levy et al., "Water and Proteins: A Love-Hate Relationship." *PNAS*, vol. 101, No. 10, Mar. 2004, pp. 3325-3326.
Madden et al., "The Antigenic Identity of Peptide-MHC Complexes: A Comparison of the Conformations of Five Viral Peptides Presented by HLA-A2." *Cell*, vol. 75, Nov. 1993, pp. 693-708.
Marsh et al., *The HLA FactsBook*, San Diego: Academic Press, 2000.
Matsumura et al., "Emerging Principles for the Recognition of Peptide Antigens by MHC Class I Molecules." *Science*, vol. 257, Aug. 1992, pp. 927-934.
Mendes et al., "Improved Modeling of Side-Chains in Proteins With Rotamer-Based Methods: A Flexible Rotamer Model." *Proteins: Structure, Function, and Genetics*, vol. 37, 1999, pp. 530-543.
Ogata et al., "Automatic Sequence Design of Major Histocompatibility Complex Class I Binding Peptides Impairing CD8$^+$T Cell Recognition." *J. Biol. Chem.*, vol. 278, No. 2, Jan. 2003, pp. 1281-1290.
Ooi et al., "Accessible Surface Areas as a Measure of the Thermodynamic Parameters of Hydration of Peptides." *Proc. Natl. Acad. Sci. USA*, vol. 84, May 1987, pp. 3086-3090.
Parker et al., "Scheme for Ranking Potential HLA-A2 Binding Peptides Based on Independent Binding of Individual Peptide Side-Chains." *J. Immunol.*, vol. 152, 1994, pp. 163-175.
Parker et al., "Peptide Binding to MHC Class I Molecules: Implications for Antigenic Peptide Prediction." *Immunol. Res.*, vol. 14, 1995, pp. 34-57.
Persson et al., "Three-Dimensional Structures of MHC Class I-Peptide Complexes: Implications for Peptide Recognition." *Archivum Immunologiae et Therapiae Experimentalis*, vol. 48, 2000, pp. 135-142.
Peters et al., "Examining the Independent Binding Assumption for Binding of Peptide Epitopes to MHC-I Molecules." *Bioinformatics*, vol. 19, No. 14, 2003, pp. 1765-1772.
Rammensee et al., "SYFPEITHI: Database for MHC Ligands and Peptide Motifs." *Immunogenetics*, vol. 50, 1999, pp. 213-219.
Rognan et al., "Predicting Binding Affinities of Protein Ligands from Three-Dimensional Models: Application to Peptide Binding to Class I Major Histocompatibility Proteins." *J. Med. Chem.*, vol. 42, 1999, pp. 4650-4658.
Rosenfeld et al., "Flexible Docking of Peptides to Class I Major-Histocompatibility-Complex Receptors." *Genetic Analysis: Biomolecular Engineering*, vol. 12, 1995, pp. 1-21.
Rötzschke et al., "Peptide Motifs of Closely Related HLA Class I Molecules Encompass Substantial Differences." *Eur. J. Immunol.*, vol. 22, 1992, pp. 2453-2456.
Rudolf et al, "Human T-Cell Responses to HLA-A-restricted High Binding Affinity Peptides of Human Papillomavirus Type 18 Proteins E6 and E7." *Clinical Cancer Research*, vol. 7, Mar. 2001 (Suppl.), pp. 788s-795s.
Ruppert et al., "Prominent Role of Secondary Anchor Residues in Peptide Binding to HLA-A2.1 Molecules." *Cell*, vol. 74, Sep. 1993, pp. 929-937.
Saper et al., "Refined Structure of the Human Histocompatibility Antigen HLA-A2 at 2×6 Å Resolution." *J. Mol. Biol.*, vol. 219, 1991, pp. 277-319.
Schapira et al., "Prediction of the Binding Energy For Small Molecules, Peptides and Proteins." *J. Mol. Recognit.*, vol. 12, 1999, pp. 177-190.
Schrauber et al., "Rotamers: To Be or Not to Be? An Analysis of Amino Acid Side-Chain Conformations in Globular Proteins." J. Mol. Biol., vol. 230, 1993, pp. 592-612.
Sidney et al., "Specificity and Degeneracy in Peptide Binding to HLA-B7-Like Class I Molecules." *J. Immunol.*, vol. 157, 1996, pp. 3480-3490.
Sipple et al., "Helmholtz Free Energies of Atom Pair Interactions in Proteins." *Folding & Design*, vol. 1, No. 4, Jul. 1996, pp. 289-298.
Smith et al., "Bound Water Structure and Polymorphic Amino Acids Act Together to Allow the Binding of Different Peptides to MHC Class I HLA-B53." *Immunity*, vol. 4, Mar. 1996, pp. 215-228.
Stern et al., "Fluctuating Charge, Polarizable Dipole, and Combined Models: Parameterization from ab Initio Quantum Chemistry." *J. Phys. Chem. B.*, vol. 103, 1999, pp. 4730-4737.
Stern et al., "Antigenic Peptide Binding by Class I and Class II Histocompatibility Proteins." *Structure*, vol. 2, Apr. 1994, pp. 245-251.
Vajda et al., "Empirical Potentials and Functions for Protein Folding and Binding." *Current Opinion in Structural Biology*, vol. 7, 1997, pp. 222-228.
van der Burg et al., "An HLA Class I Peptide-Binding Assay Based on Competition for Binding to Class I Molecules on Intact Human B Cells." *Human Immun.*, vol. 44, 1995, pp. 189-198.
Wang et al., "Further Development and Validation of Empirical Scoring Functions for Structure-Based Binding Affinity Prediction." *J. Comp-Aided Mol. Des.*, vol. 16, 2002, pp. 11-26.
Warshel et al., "Theoretical Studies of Enzymic Reactions: Dielectric, Electrostatic and Steric Stabilization of the Carbonium Ion in the Reaction of Lysozyme." *J. Mol. Biol.*, vol. 103, 1976, pp. 227-249.
Weng et al., "Prediction of Protein Complexes Using Empirical Free Energy Functions." *Protein Science*, vol. 5, 1996, pp. 614-626.
Wimley et al., "Solvation Energies of Amino Acid Side Chains and Backbone in a Family of Host-Guest Pentapeptides." *Biochemistry*, vol. 35, 1996, pp. 5109-5124.
Wolfenden et al., "Affinities of Amino Acid Side Chains for Solvent Water." *Biochemistry*, vol. 20, 1981, pp. 849-855.
Zhang et al., "Crystal Structure of the Major Histocompatiblity Complex Class I H-2K$^b$ Molecule Containing a Single Viral Peptide: Implications for Peptide Binding and T-Cell Receptor Recognition." *Proc. Natl. Acad. Sci. USA*, vol. 89, 1992, pp. 8403-8408.

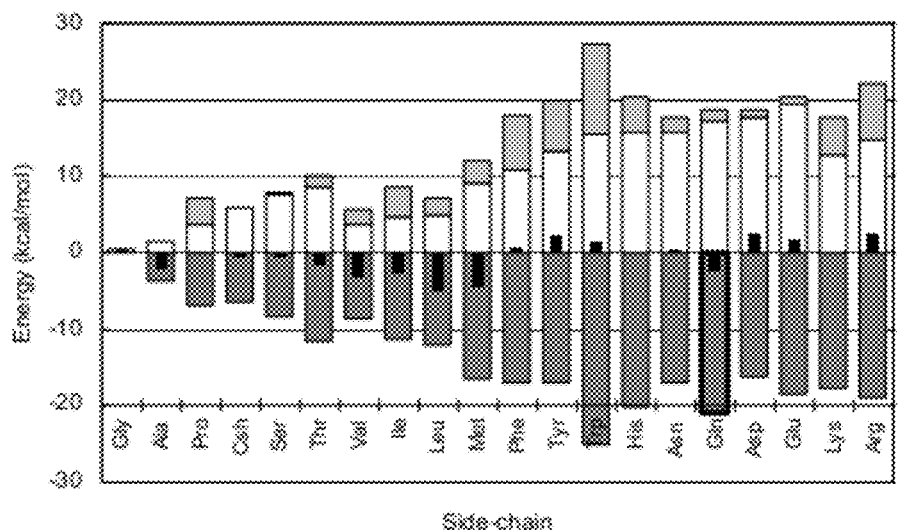
Fig. 2A
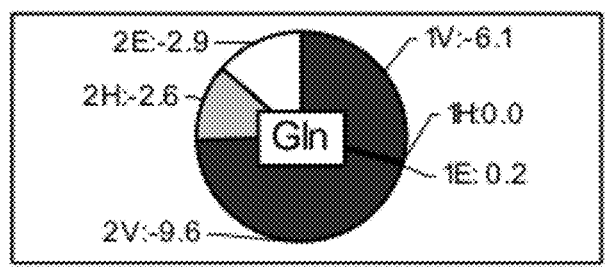
Fig. 2B
| P2 | PepScope | T | S | V | A | D | L | N | I | M | Q | Y | C | G | *E* | *H* | *P* | *F* | *R* | *W* | *K* |
|---|---|---|---|---|---|---|---|---|---|---|---|---|---|---|---|---|---|---|---|---|---|
| | Bimas | T | S | A | C | I | L | V | M | G | N | P | Q | | *D* | *E* | *F* | *H* | *K* | *R* | *W* | *Y* |
| P3 | PepScope | D | E | H | Y | M | W | F | C | A | L | V | P | Q | T | *S* | *G* | *I* | *R* | *K* | *N* |
| | Bimas | E | D | A | C | F | G | H | I | L | M | N | P | Q | S | T | V | Y | *K* | *R* | *W* |
| P9 | PepScope | Y | K | F | T | M | R | V | A | L | I | W | C | H | S | *G* | *P* | *D* | *Q* | *E* | *N* |
| | Bimas | Y | K | F | R | A | C | G | H | I | L | M | N | Q | S | T | V | W | *D* | *E* | *P* |
Fig. 3

METHOD FOR AFFINITY SCORING OF PEPTIDE/PROTEIN COMPLEXES

This application is a Divisional Application of U.S. Ser. No. 11/568,108, filed 18 Oct. 2007, which is a U.S. National Stage Application of PCT/BE2005/000052, filed 21 Apr. 2005, which claims benefit of Ser. No. 04447103.5, filed 21 Apr. 2004 in the EPO and which applications are incorporated herein by reference. A claim of priority to all, to the extent appropriate is made.

FIELD OF THE INVENTION

The present invention is related to a quantitative structure-based affinity scoring method for ligand/protein complexes such as peptide/protein complexes. More specifically, the present invention comprises a method that operates on the basis of a highly specific force field function (e.g. CHARMM) that is applied to all-atom structural representations of peptide/receptor complexes. Peptide side-chain contributions to total affinity are scored after detailed rotameric sampling followed by controlled energy refinement. The method of the invention further comprises a de novo approach to estimate dehydration energies from the simulation of individual amino acids in a solvent box filled with explicit water molecules and applying the same force field function as used to evaluate peptide/receptor complex interactions.

BACKGROUND OF THE INVENTION

Peptides are important regulatory molecules involved in a variety of biological mechanisms. Their function is generally determined by processing kinetics, interaction specificity and, more fundamentally, binding affinity. A thorough understanding of the contributions relevant for stable complex formation may form the basis of experimental rationalization, detection of novel ligands and optimization of lead compounds. Predictive structure-based methods can be very helpful, provided that they are of sufficiently high accuracy.

Structure-based binding studies face two major technical barriers. The first resides in the prediction of accurate 3D-structures for peptide/receptor complexes. Peptides are conformationally very flexible since most of their chemical bonds are subject to free rotation. A partial solution is to perform flexible docking using predefined rotamers. Yet, deviation from ideal rotameric states and small-scale flexibility due to bond angle bending present additional difficulties. Occasionally, peptides adopt variable binding modes, partly bulge out into solvent or let some flanking residues hang out of the binding site. Yet, it is often observed that one or more peptide side-chains are anchored into well-shaped pockets in the interface surface. In such cases, conformational flexibility is limited, which facilitates structure-based analysis.

The second problem is how to derive accurate binding affinities from experimental or modeled representations. Even short peptides easily contain more than a hundred atoms, making thousands of small pairwise atomic interactions. Further, ligand/receptor interfaces are rarely optimally packed and can include multiple water molecules. Finally, binding affinity depends on thermodynamic properties of the bound and free states of the molecules involved.

In view of these complications, structure-based affinity scoring methods invariably include approximations and/or a parameterization step wherein physically relevant effects are captured into tunable parameters. A distinction should be made between statistical and empirical methods. Statistical, or knowledge-based scoring methods operate on the basis of atom (or group) contact potentials derived from known protein structures. Empirical, or partitioning methods work with predefined physical energy terms, represented by parameterized mathematical equations that are optimized against experimental data. In view of the inevitable training step, validation on independent data is required. Here, it is not uncommon that methods performing relatively well on data similar to the training set are significantly less accurate on more divergent datasets or must even be retrained. Transferability therefore remains an important and delicate matter. Transferability is defined herein as the use of one and the same scoring function for different receptor/ligand systems.

The present invention is related to the binding characteristics of anchor residues within peptide ligands of receptor molecules, e.g. human leukocyte antigen (HLA) complexes. HLA class I molecules are immunologically important receptors involved in specific recognition between cytotoxic T lymphocytes and pathogen-infected cells. Pathogen-derived peptides, known as antigens, are mostly 8-10 residues long. Structural information from the Protein Data Bank (PDB) is available for an increasing number of receptor subtypes (at present about ten). Common features of these complexes are the strong interactions between receptor side-chains and the N- and C-terminal ends of the peptide backbone. The side-chains of peptide residues P2 (or, occasionally, P3) and P9 (for 9-mers) are located into well-formed pockets named B (or D) and F, respectively. Hence, the side-chain orientation of anchor residues and their structural context are relatively fixed. Yet, there is a significant variety in anchor properties among different subtypes. Finally, anchor residues are dominant contributors to total affinity and greatly determine binding specificity. For all these reasons, anchor residues in HLA class I complexes are ideally suited to develop or test novel affinity scoring methods.

The present invention relates to the identification of the physico-chemically most relevant affinity determinants. Possible contributions like contact-based potentials, weight-adapted conformational energy terms, shape complementarity, hydrophobic corrections and different entropical components may yield good results but poor transferability. Because of the danger of overparameterization, erroneous assignment of either false or redundant contributions is likely. Underparameterization, in particular of conformational strain, is another problem. The inventors therefore examined the possibility to develop a scoring function based exclusively on an established force field function. The principal advantage of force field based approaches is that different physico-chemical interactions can be computed in a consistent way.

SUMMARY OF THE INVENTION

The present invention concerns a method for determining an affinity score of a binding protein/ligand complex such as a MHC receptor/ligand complex, said score advantageously being based, advantageously being primarily or solely based on structural data and a force field.

An affinity score can equally be determined for the anchor residues of said binding protein/ligand complex such as a MHC receptor/ligand complex.

In another embodiment the present invention comprises the method according to any of the previous embodiments whereby said affinity score represents a combination of desolvation energy and protein-ligand complex energy, advantageously receptor-ligand complex energy, wherein both said energies advantageously are derived from the same force field.

Advantageously, the affinity score and method of the present invention is transferable to different protein/ligand systems, advantageously to different receptor/ligand systems, without reparameterisation.

The present invention in particular relates to a method for determining an affinity score of a protein/ligand complex, characterised in that said score is based on, advantageously primarily based on, advantageously solely based on structural data and a force field, this method comprising the steps of (a) calculating a ligand-solvent interaction energy from a structural representation of the ligand placed in a box filled with explicit solvent molecules;

(b) calculating a ligand-protein interaction energy from a structural representation of the ligand placed in the binding site of the protein; and (c) calculating said affinity score by subtracting the ligand-solvent interaction energy of step (a) from the ligand-protein interaction energy of step (b).

Preferably conformational strain energies are also taken into account. Accordingly, the present invention further relates to a method for determining an affinity score of a protein/ligand complex, characterised in that said score is based on, advantageously primarily based on, advantageously solely based on structural data and a force field, this method comprising the steps of (a) calculating a ligand-solvent interaction energy from a structural representation of the ligand placed in a box filled with explicit solvent molecules;

(b) calculating a ligand-protein interaction energy from a structural representation of the ligand placed in the binding site of the protein;

(c) calculating a conformational strain energy for the protein/ligand representation of step b; and (d) calculating said affinity score by subtracting the ligand-solvent interaction energy of step (a) and the conformational strain energy of step (c) from the ligand-protein interaction energy of step (b). Advantageously the conformational strain energy of step (c) herein is calculated as the difference between, on the one hand, the sum of the conformational energies of the ligand and protein in an unbound reference state and, on the other hand, the sum of the conformational energies of the ligand and the protein in the protein/ligand representation of step (b). It is thus possible to calculate conformational strain energies sufficiently fast and in a way that they are compatible with the force field used.

In a method according to the invention an affinity score advantageously is calculated (solely) from structural data and a force field. The force field may be any force field known in the art.

Advantageously exactly the same force field function is used to derive ligand-protein interaction energies; ligand-solvent interaction energies, also called (de)solvation energies, (de)hydration energies; and possibly also conformational strain energies. (De)solvation energies are advantageously derived from simulations of amino acid model compounds in an explicit solvent environment, for instance an explicit water environment. Potential inconsistencies between solvent terms derived from experimental data and intra-complex terms based on the force field are thus avoided. Advantageously the solvent in step (a) of the above methods exclusively consists of water molecules.

Advantageously, the protein/ligand representation of step (b) in a method according to the invention is derived from an experimentally determined structure.

Alternatively the protein/ligand representation of step (b) may be generated by computer modelling. Advantageously, the computer modelling comprises an amino acid side-chain modelling step and/or an energy minimisation step.

Advantageously the representation of the ligand in the solvent box of step (a) of a method according to the invention is derived from an experimentally determined structure.

Alternatively the representation of the ligand in the solvent box of step (a) may be generated by computer modelling.

Advantageously the computer modelling comprises an amino acid side-chain modelling step and/or an energy minimisation step.

The methods of the invention are highly suitable for affinity scoring of protein-ligand complexes or receptor-ligand complexes. The protein to which the ligand binds can be a receptor such as e.g. a MHC receptor, a HLA receptor, but it may also be an antibody. The antibody may be a polyclonal or a monoclonal antibody or a fragment thereof that is capable of forming a 3-D structure (a macromolecule) to which a ligand can bind.

Advantageously the ligand is a peptide, a small molecule or a pharmacophore. The term "ligand" in the context of the present invention can refer to part of a ligand, such as the anchor residues of a ligand. The term "ligand" can refer in particular to any part of a peptide, including a side chain, backbone moiety, chemical group, . . . via which the ligand can interact with/bind to its binding protein or receptor.

A method of the invention is highly suited to calculate an affinity score for the anchor residues of a ligand, but may also be used to determine affinity scores for non-anchor residues so that a score can be determined for the whole of a ligand.

Advantageously, experimental data are used to verify predicted results.

The scoring functions of the invention are easily transferable to different protein/ligand complexes, as demonstrated below, without the need of reparameterisation.

SHORT DESCRIPTION OF THE DRAWINGS AND TABLES

The FIG. 1 represents computed hydration energies for amino acid side-chains in a water box. Contributions for van der Waals (black bars), H-bonding (gray) and electrostatic interactions (white) are given separately. Values are further subdivided per chemical group present in a side-chain and are therefore useful as group solvation parameters (GSP). Nine different functions are considered: (1) aliphatic $C_xH_y$; (2) aromatic $C_xH_y$; (3) aromatic $N_xH_y$; (4) hydroxyl, OH; (5) sulphur/sulphydryl, S/SH; (6) charged amine, $NH_3^+$; (7) carboxyl, $COO^-$; (8) amide, $CONH_2$; and (9) guanidinium, $NHC(NH_2)_2^+$ atoms. Thus, each side-chain is composed of maximally three groups. Values for the aliphatic moieties (all residue types) are indicated by thin outlines. The second chemical moiety, if any, is indicated by thick outlines. The third moiety (only Tyr, Trp and His) again by thin outlines.

The FIG. 2A represents energy contributions calculated for different side-chains placed at P2 in the pA1a/A2 complex. White bars, desolvation energies; light gray bars, strain terms; dark gray bars, sum of intra-complex interactions. Total energies are indicated by tiny black bars; they correspond to the scores in column 3 of Table I. The FIG. 2B represents a detail of Gln interactions with the A2 receptor; 1, first group (aliphatic moiety); 2, second group (amide function); V, van der Waals; H, H-bonds; E, electrostatic energy. Numeric values are computed interaction energies in kcal/mol units. 1V:−6.1, 1H:0.0, 1E:0.2, 2V:−9.6, 2H:−2.6, 2E: −2.9.

The FIG. 3 represents a comparison of anchor profiles for HLA-A1 between PepScope and Bimas predictions. Amino acid preferences for the anchor positions indicated at the left are listed in decreasing order of preference. Strong and non-preferred residues are indicated in bold and italics, respectively. The corresponding cutoffs are −2.5 and 0 kcal/mol for PepScope and 2 and 0.1 units for Bimas.

Table I gives Predicted vs Experimental Affinities of FLSKQYMTL Mutants.

Table II shows HLA-B7 Anchor Specificity.

The invention will be described in further details in the following examples by reference to the enclosed drawings and tables, which are not in any way intended to limit the scope of the invention as claimed. The methods here described in more details for HLA receptors is applicable to other binding protein-ligand complexes.

DETAILED DESCRIPTION OF THE INVENTION

The present invention describes the development of a novel affinity scoring method here named "PepScope". The latter forms part of the EpiBase™ platform for T-cell epitope identification (pending patent application WO03/105058 which is incorporated herein by reference). The CHARMM force field was selected as the sole input function to PepScope. No parameterization steps were performed, except at the level of the protocol (e.g. the number of energy minimization steps, cutoff distances and model preparation strategy). Exactly the same force field function was used to derive (de)hydration energies from simulations of amino acid model compounds in explicit water environment. Potential inconsistencies between solvent terms derived from experimental data and intra-complex terms based on the force field were thus avoided.

To demonstrate the transferability of the scoring function, the PepScope method has been applied to four physically different HLA receptors as described in the examples section of this application. A systematic study of all natural amino acid substitutions at the anchor positions in HLA-A*0101 (A1), HLA-A*0201 (A2), HLA-A*2402 (A24) and HLA-B*0702 (B7) was performed. The predictions were compared with experimental data either from literature (A1 and B7) or from own binding assays (A2 and A24). The binding capacity of 39 nonamers FxSKQYMTx (x is any of the 20 natural amino acids) was tested on A2 and A24. The latter data are unique in that they display the anchor specificity over the entire range of possible substitutions. This has enabled the inventors to quantify not only favorable but also disruptive effects. With respect to the latter, the inventors emphasize the generally underestimated roles of desolvation and conformational strain.

The PepScope method uses only structural data and a standard force field function to score anchor residues in HLA complexes. This approach offers several advantages: (i) its independence from experimental binding data guarantees unbiased analysis with a greater sensitivity, (ii) the method is equally well applicable in cases where experimental information is scarce, and (iii) computed affinities can be thoroughly rationalized either by dissection into physical contributions or by structural inspection. Furthermore, since the method does not contain a training step, it is characterized by a great transferability. The inventors have demonstrated this by validation on four HLA receptors with divergent physical properties.

Transferability of the method was demonstrated by its application to the hydrophobic HLA-A2 and -A24 receptors, the polar HLA-A1 and the sterically ruled HLA-B7 receptor. A combined theoretical and experimental study on 39 anchor substitutions in FxSKQYMTx/HLA-A2 and -A24 complexes indicated a prediction accuracy of about ⅔ of a log-unit in Kd. Analysis of free energy contributions identified a great role of desolvation and conformational strain effects in establishing a given specificity profile.

Interestingly, the method rightly predicted that most anchor profiles are less specific than so far assumed. This suggests that many potential T-cell epitopes could be missed with current prediction methods. The results presented in this work may therefore significantly affect T-cell epitope discovery programs applied in the field of peptide vaccine development.

The PepScope method has an original approach to quantify desolvation effects. This is accomplished by in silico submersion of amino acid model compounds in explicit water, followed by standard energy minimization and proper rotameric sampling, energy calculation, averaging and selection. Combination of solvent terms with intra-complex energies results in scores devoid of systematic errors. Thus, desolvation energies derived by the said in silico method are compatible with intra-complex terms.

The PepScope scoring function basically consists of three energetic components: desolvation, direct ligand/receptor interactions and intra-complex strain (whereby the two latter components are two types of intra-complex energy). These terms are strongly affected by local conditions in a complex, the latter forming the basis of specificity. In order for a residue to be contributive, its local interactions have to compensate for unfavorable desolvation and strain. The net balance can be very delicate, especially when aromatic or polar side-chains are involved. From a modeling point of view, this imposes very high demands on the accuracy of complex models. The inventors have demonstrated that such high level of accuracy is attainable for buried anchors. It is obvious for the man skilled in the art that scoring of non-anchor residues or full peptide sequences lies in the extension of the methodology of the present invention. The PepScope method is therefore to be seen as an affinity scoring method for complete ligands.

Affinity Scoring Algorithm

Affinity scoring of anchor residues is accomplished basically by a combined side-chain rotameric search and energy refinement approach. The following steps are performed individually for all amino acid side-chains at each anchor position in all pA1a/HLA complex models.

The side-chain is introduced in standard geometry. Then, all rotamers from the same library as used in the model preparation are applied consecutively to the mutated side-chain. Dummy rotamers are used for Gly, Ala and Pro. Each rotameric variant is submitted to 800 steps conjugated gradient energy minimization. Moderate positional restraints (1 kcal/Å$^2$) are applied to the full backbone of the complex except the substituted residue and its flanking peptidic groups. The cutoff for non-bonded interactions is set to 14 Å. The following analyses are carried out on the minimized structures: computation of accessible surface area (ASA) of the side-chain rotamer, conversion of ASA into percentage buried surface area (% BSA), calculation of desolvation energy ($E_{desolv}$), computation of side-chain/receptor non-bonded interactions ($E_{inter}$) and computation of conformational strain energy ($E_{strain}$). The modeling step is concluded by selecting the rotamer r with the best total energy score ($E_{total}$) in accordance with Eq. 1.

$$E_{total} = \min_r \{E_{desolv}(r) + E_{inter}(r) + E_{strain}(r)\} \quad (1)$$

Affinity scores are calculated for all possible amino acid substitutions at the anchor positions P2 and P9 in pA1a/A2, -A24 and -B7, and positions P3 and P9 in pA1a/A1. Noise effects due to imperfections in individual models or fluctuations in the minimization path are reduced by taking the average $E_{total}$ value over three models constructed per receptor type.

The PepScope scoring function by default subdivides each of the three global energy terms into more elementary components, primarily for the sake of comprehensibility. In the case of the desolvation terms, this also enables working with functional group solvation parameters (GSPs) rendering desolvation terms conformation sensitive. The global energies are subdivided according to Eqs. 2-4; the contributions are discussed in the next paragraphs.

$$E_{desolv} = -\Sigma_i \% BSA(i) \times GSP(i) \quad (2)$$

$$E_{inter} = \Sigma_i \{E_{vdw}(i) + E_{hbo}(i) + E_{ele}(i)\} \quad (3)$$

$$E_{strain} = E_{rec} + E_{pep} E_{self} \quad (4)$$

In Eqs. 2 and 3, i denotes one of the chemical functions present in the mutated side-chain (defined in the legend to FIG. 1). Any given side-chain type is described by maximally three chemical groups. All side-chain types comprise group 1, defined as the aliphatic moiety. The subdivision of $E_{desolv}$ and $E_{inter}$ into group contributions is justified in view of the additive nature of surface areas and nonbonded energy terms.

An important aspect of PepScope is that GSP values are derived de novo, i.e. from simulations of amino acid reference conformations in a spherical water box filled with explicit water molecules. This approach is expected to yield $E_{desolv}$ energies that are maximally consistent with the intra-complex terms $E_{inter}$ and $E_{strain}$, because both types of energy are based on the same parameters and equations from the CHARMM force field. The PepScope solvent model is therefore designated "internal" as opposed to "external" models based on experimental group or atomic solvation parameters.

The direct side-chain/receptor interactions ($E_{inter}$) are the most obvious contributions. They consist of van der Waals interactions quantified by a "6-12" Lennard-Jones potential ($E_{vdw}(i)$), H-bonds represented by a "10-12" potential ($E_{hbo}(i)$) and electrostatic interactions calculated by a Coulombic equation with a distance-dependent dielectric constant ($E_{ele}(i)$). Van der Waals and H-bond interactions are computed with a cutoff distance of 16 Å while 25 Å is used for electrostatic energy. Computed values for $E_{vdw}(i)$, where i refers to aromatic or guanidinium groups, are reduced to 80% of the original value to avoid overprediction.

The strain term $E_{strain}$ stands for "every increment in energy due to the mutant side-chain, except direct interactions". Computing it by comparing energies before and after minimization would mostly result in "negative increments" due to global structural drift independent of the substitution. Therefore, strain contributions are computed on the mutated and minimized structure and compared with the same terms derived from the minimized pA1a/HLA structure ("mutant" strain minus "Ala" strain). A first component of $E_{strain}$ is $E_{rec}$, the strain energy residing in the receptor, more precisely within the set of atoms closer than 15 Å from the $C_\beta$-atom of the mutated position. A second component is $E_{pep}$, the strain felt by the entire poly-Ala peptide (i.e., the full peptide minus the substituted residue). This term includes both the self energy of the peptide and its interactions with the receptor. The third component is $E_{self}$, the self tension of the mutation, including all bonded and nonbonded energies within the mutated residue (side-chain, main-chain and flanking peptide groups). In contrast to $E_{rec}$ and $E_{pep}$, $E_{self}$ is measured relative to the self energy of the same amino acid in the water box, and not relative to the minimized pA1a/HLA structure. Occasionally, one or more of the strain terms assume unrealistically high values. However, rather than imposing general strain maxima, the full score is always calculated first (Eq. 1) and then, if higher, truncated at 3.0 kcal/mol.

Computation of Group Solvation Parameters.

Acetylated and aminomethylated amino acids are placed at the center of a spherical water box with a radius of 37 Å and containing 6840 molecules in a TIP4P configuration. Side-chain conformations are retrieved from the same rotamer library as used in the preparation of complex models. Rotamers are considered one by one, for all 20 natural residue types. For each rotamer, the dimensions of the system are reduced by retaining only the water molecules in a 20 Å layer around the solute. Next, all overlapping water molecules are removed. Overlap is defined as a distance between any solute-water atom pair smaller than the sum of their respective van der Waals radii, minus a tolerance of 1 Å. The system is subsequently energy minimized by performing 200 steps conjugated gradient minimization using a 14 Å cutoff and 10 kcal/Å$^2$ positional restraint on the water oxygen atoms (not on the hydrogens, nor on the solute atoms). The whole procedure is repeated 100 times per rotamer using slightly different initial placements (a uniform random offset relative to the center of the sphere was applied to the X-, Y- and Z-coordinates of the solute, sampled from the interval −2,+2 Å). For each rotamer, the 25 solutions having the best total side-chain/water interaction are retained and their values are averaged. Finally, the rotamer with the lowest average energy is retained for each residue type. FIG. 1 shows the computed energies, subdivided into van der Waals, H-bonding and electrostatic interactions for each chemical group.

Development of an Internal Desolvation Model

The energetic cost associated with the liberation of a ligand from a solvent environment is very large in comparison with the net gain in free energy upon binding to a receptor. Hence, the model used to quantify desolvation effects is critical for success. The known anchor preferences of different class I receptor subtypes are described reasonably well by the CHARMM force field but only for hydrophobic and not for polar residues. Dissection of intra-complex interaction energies into contributions from separate functional groups shows that the interactions from polar groups and, to a lesser extent, also aromatic atoms are much too strong to be correlating with experimental affinities. The interaction energies that are to be compensated by the solvent model are typically around 20 kcal/mol for buried polar side-chains. Since this value is much larger than experimental transfer free energies from the vapor phase to water, one could question the compatibility of such data with the force field used in the present invention. The inventors therefore analyzed solute-solvent interactions of the 20 natural amino acid residues, in silico submerged into a water box. The energetic analysis was performed separately for van der Waals, H-bonding and electrostatic contributions and for the different chemical functions present in the side-chain, using the CHARMM force field.

FIG. 1 shows that the aliphatic residues Ala, Pro, Val, Ile and Leu have small, negative hydration energies arising almost purely from van der Waals interactions. They remain below 5 kcal/mol in absolute value. In contrast, polar side-chains other than Ser and Thr make about 3 to 4 times stronger interactions, roughly between −13 kcal/mol (Lys) and −19 kcal/mol (Glu). Thus, even nonpolar side-chains have favorable hydration energies but the latter are much smaller than those of polar side-chains.

All OH groups (Ser, Thr, Tyr) have similar values: negligible van der Waals and about −3 kcal/mol H-bonding and electrostatic interactions.

Amide and carboxylate groups have nearly identical H-bonding and electrostatic interactions (about −5 and −7 kcal/mol, respectively). This may seem surprising in view of the carboxylate groups carrying a net charge, as opposed to amide groups. Apparently, the OC- and the two HN-dipoles in an amide group are almost equivalent to the two OC-dipoles carrying negative charges in carboxylates. Compared to OH-groups, amides and carboxylates have much stronger van der Waals (~7×), slightly stronger H-bonds (~1.5×) and much stronger electrostatics (~2.5×). Very similar results are obtained for the joint $N_\delta$-/$N_\epsilon$H-groups from the His imidazole ring. Considering that these contributions to hydration energy must be overcompensated in a complex in order for the corresponding groups to have a net stabilizing effect, the values obtained are very large.

The charged amine of Lys and the guanidinium function of Arg both have H-bonding terms similar to that of an OH-group (~−3.0 kcal/mol). Also the electrostatic terms hardly differ: that of the guanidinium group is ~1 kcal/mol smaller than for OH. This is yet another unexpected result in view of both Lys and Arg being charged and possessing much more dipoles than OH-containing residues. The main difference with OH-functions is observed at the level of van der Waals interactions: the Lys and Arg polar groups respectively have 2.5 and 12-fold stronger van der Waals interactions than OH.

The S-/SH-groups of Cys and Met are poor H-bond formers and make weak electrostatic interactions in water. In contrast, the van der Waals contribution is exceptionally large (−3.3 kcal/mol), which is obviously due to the greater polarizability of S-atoms. Finally, aromatic atoms have a relatively simple hydration profile: no H-bonds, very weak electrostatics and regular van der Waals interactions of about −1.3 kcal/mol per heavy atom.

These computed hydration energies are to be considered as group solvation parameters (GSPs). The energetic cost associated with (partial) dehydration of a side-chain i consisting of functional groups j, $E_{dehyd}$, can be computed by Eq. 5 (analogous to Eq. 2):

$$E_{dehyd}(i) = -\Sigma_j GSP(i,j) f_b(i,j) \quad (5)$$

where $f_b(i,j)$ is the fraction of buried surface area for group j of side-chain i, calculated as $$f_b(i,j) = (A_r(i,j) - A_c(i,j))/A_r(i,j) \quad (6)$$

and where $A_r(i,j)$ and $A_c(i,j)$ are the group ASAs in the reference state (here, the rotamer selected in the water box simulations) and in a complex, respectively.

Affinity Scoring Issues

Accurate modeling of the conformation of anchor residues in peptide/receptor complexes is not very complicated, provided that models are prepared with state-of-the-art methodology, that the conformational space of the anchor side-chains is thoroughly explored, and that the structures are adequately refined using appropriate restraints. A greater problem however is to derive affinities from structural data. It is a real challenge to develop a robust, generally applicable scoring method that does not require reparameterization for different systems, i.e. a transferable method.

The invention has contributed to the affinity scoring problem in several ways.

In one embodiment, the inventors have demonstrated that a standard force field is useful as the basis of a scoring function, provided that it is supplemented with a suitable solvent function.

In another embodiment, a method was developed to derive desolvation energies on the basis of the same force field that is used to evaluate intra-complex energetic contributions. The hypothesis that such "internal" model would be preferred over "external" approaches because of a higher consistency in the calculated energies, is confirmed by the results.

Yet another embodiment of the present invention applies a fully additive energy model, wherein diverse contributions from van der Waals interactions, H-bonds, electrostatics, and different types of bonded energy are calculated separately and then simply added up in order to obtain final scores. As a matter of fact, there are two aspects to the problem of (non-) additivity: (i) the question whether a simple pairwise-additive force field function is of sufficient accuracy, and (ii) in the case of multi-residue peptide ligands, the assumption that each residue contributes independently to total affinity. Concerning the first type of non-additivity it is likely that the errors made by a pairwise atomic force field function are not significant enough to urge for a more sophisticated approach. Regarding the assumption of independence between different parts of a ligand, this is circumvented in the present invention by focussing on the peptide/MHC anchor residues, the backbone of which is held in a stiff grip by the receptor, and the side-chains of which are relatively isolated. This way, the affinity scoring problem could be studied without interference from global, non-linear packing problems.

Another embodiment of the present invention demonstrates that the net ligand binding free energy is fundamentally a delicate balance between very large components: free energy of desolvation and free energy of binding. When decomposing the latter into direct ligand/receptor interactions and induced strain, one arrives at two positive and one negative contribution. FIG. 2 illustrates their mutual proportions, computed for all amino acid side-chains at position P2 in HLA-A2. Given the good correlation with experiment (Tables I and II), the individual terms should be meaningful. However, the implications from the point of view of a modeler are, to put it mildly, enormous. The net binding energy of an "average" side-chain in a "typical" receptor pocket amounts at best about 25%, but mostly around 10%, or less, of the corresponding intra-complex interaction terms. This means that a 10% error in any of the independent contributions is likely to destroy the correlation with experiment. Failure to simulate a single, relevant H-bond (or the generation of a false H-bond) distorts the computed interaction energy by 1.5 kcal/mol in H-bonding and roughly an equal amount in electrostatic energy; this is equivalent to more than 1 log-order in Kd.

The present invention focuses on anchor residues, of which the conformation is strongly imposed by the receptor. In contrast, full-length (octa- to decameric) HLA class I binding peptides are characterized by a significant degree of flexibility near the middle part. Scoring of full peptide sequences is possible on the basis of the scoring function of the present invention. Non-anchor residues are in general contributing weakly to total affinity. Exposed residues remain largely hydrated but cannot benefit from strong interactions. Buried side-chains are more difficult: by definition, they pay the full dehydration price but they are usually located in regions of lower atomic density, which leads to reduced (van der Waals) interactions. Assuming that they can bind free of strain, the interactions and hydration energies of polar side-chains are, as a rule of thumb, similar in size. For aromatic and aliphatic side-chains there usually remains a small net profit. This explains the overall slight preference for apolar residues at buried non-anchor positions (mostly P3 and P7). Thus, buried polar side-chains in low-density regions generally stand no chance against non-polar ones, unless they are further stabilized by favorable electrostatics or H-bonds, potentially also mediated by structured water molecules. The technical complexity of modeling and scoring non-anchor residues is therefore very high, but fundamentally the same rules apply. The present invention on conformationally more restrained anchor residues can therefore be of great help in quantifying the contributions that are relevant to total affinity.

EXAMPLES

To demonstrate the transferability of the scoring function, the PepScope method has been applied to four physically different HLA receptors as described in the examples section of this application. A systematic study of all natural amino acid substitutions at the anchor positions in HLA-A*0101 (A1), HLA-A*0201 (A2), HLA-A*2402 (A24) and HLA-B*0702 (B7) was performed. The predictions were compared with experimental data either from literature (A1 and B7) or from own binding assays (A2 and A24). The binding capacity of 39 nonamers FxSKQYMTx (x is any of the 20 natural amino acids) was experimentally tested on A2 and A24. The latter data are unique in that they display the anchor specificity over the entire range of possible substitutions. This has enabled the inventors to quantify not only favorable but also disruptive effects. With respect to the latter, the inventors emphasize the generally underestimated roles of desolvation and conformational strain.

The binding specificity of peptide/HLA complexes is strongly determined by peptide anchor positions. Yet, the anchor preferences for most HLA subtypes remain poorly characterized. The inventors showed that many commonly accepted profiles are skewed in the sense that they contain false positive and, especially, false negative information. The binding capacities of Trp and Met are generally undervalued. Small, polar side-chains (e.g. Ser, Thr) are usually assigned neutral values in Bimas and Syfpeithi scoring matrices while in reality their binding strength is highly variable: relatively strong at A2-P2, A2-P9, A1-P2 and A1-P9 but prohibitive at A24-P9, B7-P2 and B7-P9. In general, all current binding motifs and profiles have difficulties in correctly appreciating anchor residues with intermediate binding capacity. Another observation is that true binding profiles are usually broader, i.e. less specific, than assumed thus far.

Example 1

Model Preparation

The preparation of model complexes depends on the availability of template structures in the Protein Data Bank. If one or more tertiary structures for a given HLA subtype are known, a selection is made primarily on the basis of crystallographic resolution. Additional criteria such as R-factor, length of the bound peptide, experimental affinity of the latter, width of the binding groove, etc., are considered as well. For A2 1DUZ was selected as the starting template. Since no exact templates were available for A1, A24 and B7, these had to be modeled. First, a structure was selected from the PDB using the same criteria as for A2, considering also the sequence similarity of receptor residues in contact with the peptide. The following template structures were chosen: 1HSB (type Aw68) for A1, 1DUZ (type A2) for A24 and 1A9E (type B35) for B7. The coordinates for amino acid residues 1-181 (the $\alpha_1\alpha_2$-domain) and the extant peptide were extracted from the files. Water molecules were ignored in this study. The truncated peptide/HLA complexes were submitted to 200 steps unrestrained steepest descent energy minimization.

In a next step, the substitutions required to construct a desired HLA sequence were introduced and modeled by the FASTER algorithm as described in pending patent application WO01/33438 which is incorporated herein by reference, and as described by Desmet et al. (Proteins, 2002, ref 40). Briefly, the peptide was temporarily removed from the complex and the mutations were performed in standard geometry. The FASTER algorithm was then applied to search for the best global packing arrangement of the substituted side-chains, using a rotamer library containing 899 conformational states for the 20 natural amino acid side-chains. The structure with the best global conformational energy was selected and refined by an extra 200 steps unrestrained steepest descent energy minimization. The original peptide was finally placed back as poly-Ala with the original backbone coordinates (likewise for the 1HSB-based model containing only the first three and last two peptide residues). The resulting model was stored as input data for the docking algorithm. The homology modeling step was skipped for HLA-A2.

In a further step, a high affinity peptide was docked into each HLA model by means of a flexible peptide docking algorithm, as described in Desmet et al (FASEB J). Briefly, the poly-Ala peptide was replaced by the sequence YTAVVPLVY for A1, FLSKQYMTL for A2 and A24, and FPVRPQVPL for B7. Bond lengths and angles, also for the main-chain, were initialized in standard geometry to avoid structural bias. The docking algorithm was then instructed to rebuild the peptide from the N-towards the C-terminus Limited translation (max. 1 Å) was allowed. The same backbone-dependent rotamer library was used as before. All groove side-chains with rotatable bonds were kept flexible during the docking. Typically, the docking algorithm identifies 50 to a few hundreds of energetically favorable complex structures. For the present study on anchor residues, only three structures per receptor type were needed. They were selected from the top-10 docking solutions, considering aspects like general packing quality, peptide backbone variation and receptor side-chain conformation. The selected complex structures were thoroughly energy minimized by 800 steps unrestrained conjugated gradient minimization. Finally, all peptides were again mutated into poly-Ala. The resulting structures, referred to as pAla/HLA models, were stored as input data for the scoring algorithm.

Example 2

Peptide Binding Assays $IC_{50}$ values were determined using a cell-based assay, largely according to van der Burg et al, Hum Immunol 1995; 44:189-98 and Kessler et al, Hum Immunol 2003; 64:245-55. Briefly, immortalized B-cells displaying HLA-A*0201 or HLA-A*2402 homozygously (VOSE EBV (A*0201, B*4402, Cw*0501/0711) and HATT EBV (A*2402, B*4801, Cw*0801/1202) are stripped of their self peptides, followed by equilibrium binding of test peptide in competition with fluorescent reference peptide (FLPSDC(5Fluorescein)FPSV for A2 and RYLKC(5Fluorescein)QQLL for A24). A 10-point concentration range of test peptide is used for each measurement, typically in 2-fold increments from 62.5 nM to 32 µM, in a constant background of 30 nM reference peptide. Adapted ranges were used for excellent binders (minimal concentration 7.8 nM) and weak binders (maximal concentration 128 µM). 50% inhibitory concentrations ($IC_{50}$-values) were calculated as averages obtained from at least 3 independent measurements, i.e. from different cell preparations and peptide dilutions. Test peptides >95% pure (Thermo Electron GmbH) were stored at 10 mM in DMSO at −20° C. Cysteine-containing peptides were stored at 10 mM in 1 mM DTT DMSO. DTT did not affect binding of FLSKQYMTL control peptide but significantly improved binding and reproducibility for FCSKQYMTL and FLSKQYMTC on both A2 and A24 (not shown). $IC_{50}$-values were converted to binding free energies (AG) using the relationships $$Kd = IC_{50} Kd_{ref}/c_{ref} \quad (7)$$

and $$\Delta G = RT \ln(Kd) \quad (8)$$

where $Kd_{ref}$ and $c_{ref}$ are the dissociation constant and formal concentration of the reference peptide, respectively. The $Kd_{ref}$ values were derived from an independent binding assay in which the fluorescence intensity was measured as a function of increasing concentrations of reference peptide. Nonlinear curve fitting using a single-site binding scheme gave approximate Kd's of 3 nM for the A2 and 30 nM for the A24 reference peptides, respectively.

Example 3

Affinity Scoring of HLA-A2 Complexes

HLA-A*0201 (A2) is one of the most extensively studied peptide binding receptor molecules. It is known to show a strong preference for peptide ligands having Leu at position P2 and Val or Leu at P9. The modeling of all 20 natural amino acid residues at the anchor positions P2 and P9 was performed systematically for the three pA1a-A2 models. FIG. 2 shows the averaged scoring values for position P2 in pA1a-A2. Total affinity scores have been dissected into the three major energetic components: desolvation energy, side-chain/complex interaction (including interactions with all pA1a residues but the mutated one) and "local strain" (including strain within the mutant residue). All values are expressed in units of kcal/mol, i.e. the units of the force field equations.

A striking observation from FIG. 2 is that direct side-chain/complex interactions are very large: for 50% of the residues they lie in the range −15 to −20 kcal/mol. It is seen that most of the side-chains "larger than Leu" have similar interactions with values around −17 kcal/mol. The smaller side-chains, most of which are aliphatic, have variable interactions ranging from 0 (Gly) to −12 kcal/mol (Leu). Thus, in absence of any compensatory effects, pure force field derived energies would predict aromatic and polar side-chains to be largely preferred over aliphatic residues at position P2 in A2 complexes.

Rather, the opposite is true: peptides binding strongly to A2 mostly have Leu, Met, Ile and sometimes Val, Ala or Thr at position P2. FIG. 2 shows that the explanation is to be found at two levels, i.e. the compensatory desolvation and strain terms. From FIG. 1 it followed that polar and aromatic side-chains are characterized by relatively large desolvation energies. The latter appears to be the primary reason for Ser, Asn, Asp and Glu to be undesired. Yet, the prohibitive nature of various other side-chains can be explained only by an additional compensatory component. Here, this is found to be the strain induced in the receptor by ill-fitting side-chains. The latter is applicable mainly to the aromatic Phe, Tyr, Trp, His and the basic Lys and Arg side-chains. Even the aliphatic Val, Ile, Leu and, especially, Pro induce some tension in their environment.

Gln is the sole polar side-chain that is reasonably well accepted in the receptor pocket at P2. FIG. 2 shows that Gln can be accommodated almost free of strain, but the desolvation cost is large (17.2 kcal/mol). Yet, Gln seems to have no problem in compensating for this by making exceptionally favorable interactions. FIG. 2B shows more detail. The aliphatic part of its side-chain interacts favorably with the pocket residues, almost exclusively through van der Waals terms. The amide group contributes even better: −9.6 (2V), −2.6 (2H) and −2.9 (2E) kcal/mol from van der Waals, H-bonds and electrostatic interactions. The total van der Waals interaction in the complex is −15.7 kcal/mol or roughly three times stronger than in the water box. In itself this is not an exceptional situation for buried, well-packed side-chains, including the polar ones. What really makes the difference is the ability of Gln to form two nearly ideal H-bonds, one between the first of its two amide $H_{\in}$ atoms and Glu A63.$0_{\in}$ and the other between the second amide $H_{\in}$ and the backbone A63.O atom. Only Lys can make the same two H-bonds, but this occurs at the cost of a considerable strain of 5 kcal/mol distributed in proportions of 2:1:2 over side-chain self, peptide pA1a energy, and receptor tension, respectively. Csh (cystein), Ser, Thr and Asn can only make 1 H-bond, which is apparently not sufficient to make them preferred residues.

The net result of the delicate balance is shown by the tiny black bars in FIG. 2. When plotted on a scale suitable to display the individual contributions, the total energy score almost vanishes (the total energy often amounts to less than 10% of the direct side-chain/receptor interaction). Pending the experimental validation below, the top-10 ranked residues (L-M-V-I-Q-A-T-S-C-K) correlate well with those of the popular Bimas scoring matrix, (L-M-I-Q-V-E-A-T-C-G). Only Glu at rank 6 in the Bimas series is in disagreement with the method of the present invention ranking Glu as the fifth worst type at P2 in A2. It will be seen that Glu in the Bimas matrix is a false positive.

Experimental Validation for A2

Validation of the predicted binding capacity was achieved by direct comparison with experimental affinities obtained for a series of systematic P2 mutants of a selected peptide. The nonameric peptide FLSKQYMTL from Hepatitis B virus polymerase, residues 676-684, was chosen because of its cross-reactivity between A2 and A24, as predicted by the full-length peptide scoring method which is part of the EpiBase™ platform.

Since experimental binding free energies were obtained for full-length peptides and expressed in kJ/mol, while predicted scores are for single residues in kcal/mol, a calibration step was required. Raw predicted scores (E) were converted to calibrated scores (E') by the equation $$E'(\text{kJ/mol})=a+b\,E(\text{kcal/mol}) \quad (9)$$

where a is the intercept and b the slope of the least squares regression line of the correlation plot. For the P2 mutants, the slope of the regression line (b) equaled 2.44 kJ/kcal and the intercept was −33.3 kJ/mol. The latter value is a measure for the affinity contributed by the peptide minus the substituted side-chain.

Table I shows the data for the wild type peptide FLSKQYMTL and all 38 P2 and P9 substitutions. The experimental data confirm the potential of Leu at P2 for strong binding. The Met and Ile variants essentially bind with the same affinity. Val and Gln at P2 also allow strong binding. These data are greatly consistent with what is known about the P2 preference of A2 binding peptides. However, the dataset further shows that Thr, Ala, Gly and Ser are feasible residues as well, something which is rarely recognized. Even the Csh and Phe variants have a dissociation constant that is less than 1 log-order worse than the wild type (1 logKd=5.74 kJ/mol). Only Tyr, Arg, Lys, Glu, Pro, Asp and Trp are truly disruptive (logKd more than two units higher than wt).

TABLE I

Predicted vs Experimental Affinities of FLSKQYMTL[a] Mutants

| A2 | | | | | | | | | | A24 | | | | | | | | | |
|---|---|---|---|---|---|---|---|---|---|---|---|---|---|---|---|---|---|---|---|
| P2 | | | | | P9 | | | | | P2 | | | | | P9 | | | | |
| AA | $G_{exp}$ | Score | $G_{pr}$ | Error | AA | $G_{exp}$ | Score | $G_{pr}$ | Error | AA | $G_{exp}$ | Score | $G_{pr}$ | Error | AA | $G_{exp}$ | Score | $G_{pr}$ | Error |
| L | −42.1 | −4.8 | −45.1 | −2.9 | M | −42.7 | −3.3 | −40.5 | 2.2 | W | −47.0 | −6.2 | −47.2 | −0.1 | W | −44.4 | −4.5 | −40.1 | 4.3 |
| M | −41.6 | −4.4 | −44.1 | −2.5 | V | −42.2 | −4.2 | −41.8 | 0.4 | F | −45.2 | −4.5 | −43.8 | 1.4 | F | −44.4 | −4.2 | −39.0 | 5.5 |
| I | −41.3 | −2.7 | −40.0 | 1.3 | L | −42.1 | −3.3 | −40.5 | 1.6 | Y | −44.7 | −5.3 | −45.4 | −0.7 | I | −41.4 | −4.2 | −39.0 | 2.4 |
| V | −40.5 | −3.2 | −41.1 | −0.5 | A | −41.8 | −2.0 | −38.8 | 3.0 | M | −44.3 | −4.0 | −42.8 | 1.5 | L | −39.7 | −4.0 | −38.2 | 1.5 |
| Q | −40.1 | −2.4 | −39.2 | 1.0 | I | −41.3 | −2.5 | −39.4 | 2.0 | Q | −43.2 | −1.2 | −36.9 | 6.2 | M | −36.7 | −4.1 | −38.6 | −1.9 |
| T | −39.7 | −1.4 | −36.6 | 3.0 | T | −40.2 | −4.4 | −42.2 | −1.9 | A | −42.1 | −1.7 | −37.9 | 4.2 | V | −32.6 | −2.3 | −32.1 | 0.5 |
| A | −39.5 | −2.1 | −38.4 | 1.0 | F | −40.2 | 0.1 | −35.7 | 4.5 | G | −39.8 | 0.1 | −34.3 | 5.5 | Y | −32.4 | −1.6 | −29.5 | 2.9 |
| G | −39.3 | 0.5 | −32.2 | 7.0 | S | −38.8 | −1.8 | −38.3 | 0.4 | L | −39.7 | −3.9 | −42.5 | −2.8 | H | −30.8 | 1.0 | −20.0 | 10.8 |
| S | −38.6 | −0.5 | −34.5 | 4.1 | C | −38.7 | −0.6 | −36.7 | 1.9 | I | −39.4 | −3.4 | −41.4 | −1.9 | C | −27.4 | −1.1 | −27.8 | −0.4 |
| C | −37.1 | −0.5 | −34.5 | 2.6 | G | −36.9 | −0.3 | −36.3 | 0.6 | V | −38.6 | −3.1 | −40.9 | −2.3 | A | −26.9 | −1.6 | −29.6 | −2.8 |
| F | −36.6 | 0.8 | −31.4 | 5.2 | W | −36.5 | 3.0 | −31.6 | 5.0 | T | −37.9 | −1.2 | −36.9 | 1.0 | G | −24.6 | 0.3 | −22.4 | 2.2 |
| N | −35.7 | 0.5 | −32.0 | 3.7 | Q | −35.8 | −1.5 | −38.0 | −2.2 | S | −36.7 | −0.3 | −35.1 | 1.7 | Q | −18.6 | 0.7 | −21.3 | −2.6 |
| H | −33.8 | 0.1 | −33.1 | 0.7 | P | −35.1 | −0.3 | −36.3 | −1.1 | H | −34.8 | 0.1 | −34.2 | 0.6 | N | −18.4 | 3.0 | −12.7 | 5.7 |
| Y | −29.7 | 2.2 | −28.0 | 1.6 | H | −34.9 | 0.4 | −35.3 | −0.4 | C | −33.1 | −0.7 | −35.9 | −2.9 | T | −18.4 | −0.9 | −27.0 | −8.6 |
| R | −27.6 | 2.4 | −27.4 | 0.2 | N | −34.1 | 0.3 | −35.4 | −1.4 | N | −32.7 | 1.8 | −30.6 | 2.1 | S | −18.3 | −0.7 | −26.3 | −7.9 |
| K | −27.0 | 0.1 | −33.2 | −6.2 | Y | −33.7 | 3.0 | −31.6 | 2.2 | R | −31.9 | 1.0 | −32.4 | −0.4 | K | −18.3 | −0.4 | −25.0 | −6.7 |
| E | −26.5 | 1.8 | −28.9 | −2.5 | K | −30.3 | −1.6 | −38.1 | −7.8 | P | −30.0 | 0.3 | −33.9 | −3.8 | R | −18.2 | 0.5 | −21.9 | −3.7 |
| P | −26.1 | 0.2 | −32.9 | −6.9 | E | −30.0 | 3.0 | −31.6 | −1.6 | E | −29.7 | 1.8 | −30.6 | −0.9 | P | −18.2 | 1.3 | −19.1 | −0.9 |
| D | −23.8 | 2.5 | −27.2 | −3.4 | D | −29.8 | 3.0 | −31.6 | −1.8 | K | −29.0 | 0.0 | −34.4 | −5.4 | E | −17.4 | 0.4 | −22.1 | −4.7 |
| W | −23.0 | 1.5 | −29.6 | −6.7 | R | −28.1 | 1.5 | −33.8 | −5.7 | D | −28.8 | 1.3 | −31.7 | −2.9 | D | −17.2 | 3.0 | −12.7 | 4.5 |
| | | | σ: 3.9 | | | | | σ: 3.1 | | | | | σ: 3.1 | | | | | σ: 5.0 | |

AA, amino acid placed at the indicated anchor position (P2/P9,) of the peptide FLSKQYMTL in the indicated complex (A2/A24);
ΔG$_{exp}$, experimental binding free energy in kJ/mol;
Score, uncalibrated affinity score in kcal/mol;
ΔG$_{pr}$, calibrated affinity in kJ/mol;
Error, difference between ΔG$_{exp}$ and ΔG$_{pr}$.
Values <−3 kJ/mol are given in bold;
values >3 kJ/mol are underlined;
σ, standard deviation of Error values.

The predictions follow the observed trends well. The top-5 best ranked peptides (Leu, Met, Val, Ile, Gln) exactly coincide with the experimental top-5. The moderately binding Gly, Ser and Phe mutants are underpredicted by approximately 1 logKd in magnitude. The opposite holds for the disruptive residues Lys, Pro and Trp although the predicted values are certainly not suggestive of favorable interaction. All other predictions are correct to within about 0.5 logKd. The overall standard deviation of the difference between predicted and experimental binding energy is 3.9 kJ/mol (~2/3 logKd).

The same theoretical and experimental analysis was performed on the second anchor position P9. Here again, the best peptides contained the well-known motif residues Val, Leu or Met. More surprising was the observation that Ala, Ile, Thr, Phe, Ser and Csh substitutions caused a reduction in affinity compared to wt of less than ~0.5 logKd. Especially Phe and Ser are usually considered prohibitive. Further, Gly and Trp are also presumed to be disruptive, but they do fall within the 1 logKd range from wt. Truly prohibited at P9 (wt+2 logKd) are only the charged residues Lys, Glu, Asp and Arg.

The P9 predictions are generally of the same or even slightly better quality than for P2. Only the value for Lys is predicted with an error larger than 1 logKd (in the false positive sense). A similar yet smaller error is observed for Arg. Underpredicted (in the false negative sense) are Trp and Phe which experienced a relatively high strain in the models (12.1 and 5.6 kcal/mol, equivalent to 29.5 and 13.7 kJ/mol, respectively; the models were probably not fully relaxed). All other residue types were predicted with an error less than ~0.5 logKd. The global standard error was 3.1 kJ/mol. Interestingly, many features that have not been recognized before were correctly predicted: (i) Val is not the best possible residue at P9, (ii) Met, Leu, Ala and Ile are almost equally preferred, (iii) 11 other residue types (50%) bind with lower but non-prohibitive strength. Analysis of the structural data showed that all but the aromatic side-chains can be accommodated free of strain into a medium-sized, mainly hydrophobic pocket (the F pocket). In the case of Phe and Trp, the computed strain was probably even overestimated. Moreover, Csh, Ser, Thr, Asn and Gln can form one ideal H-bond. Though not enough for strong binding, this evidently helps to broaden the specificity profile. The results are supported by the systematic survey of Rudolf et al who checked the A2 affinity of all possible 9-mers derived from HPV-18 E6 and E7 proteins. Fifteen out of the 247 peptides (6%) had a Kd below 1 μM but only 4 had Val at P9, 4 other had Leu, 1 Ile, and 6 had a non-standard anchor residue. In conclusion, the specificity profile at the anchor residues in A2 is well represented by the predictions and much more permissive than so far assumed.

Example 4

Binding Specificity of A24

HLA-A*2402 (A24) is another abundant MHC class I receptor with similar hydrophobicity as A2 but a significantly different (presumed) specificity profile. The anchor positions also appear at positions P2 and P9 but the consensus motif is P2(Y/F),P9(L/F/I/M) or P2(Y/F),P9(F/W/I/L). Both specificity pockets are considerably larger than in A2. For the pocket at P2, this is mainly due to the Phe→Ser mutation in the receptor at residue A9, while the Leu→Ala mutation at A81 can be held responsible for the larger F-pocket at the peptide C-terminus. The Asn at A77 (i.s.o. Asp) also tends to form a H-bond with Tyr-A116, which rigidifies part of the pocket wall.

The predictions suggested two interesting possibilities, namely, (i) that there is an overall similarity between the anchor preferences of A2 and A24, and (ii) that Trp is the most preferred residue at both anchor positions. The latter is completely overlooked in the Bimas and Syfpeithi scoring matrices and partially in the motif analysis. Also, the idea that A24 would be compatible with the A2-motif, with additional preference for bulky aromatic anchors is not known. Therefore an A24 binding assay was set up to test the same 39 P2 and P9 mutants of FLSKQYMTL on this receptor.

The experimental data in Table I confirmed the expectations: the A2-P2 preferred residues Met, Gln, (Ala), (Gly), Leu, Ile and Val and the A2-P9 preferred Ile, Leu and Met (not Val) have similar affinities for A24. Also the polar residues show the same disruptive character. Moreover, aromatic side-chains (with the exception of Tyr at P9) are contributing very strongly to affinity, a feature that is specific to A24. Trp is the "winner" at both positions P2 and P9, which is in agreement with the predictions but not with the presumed A24 motif. It is possible that the lower intrinsic amino acid frequence of Trp can be held responsible for the gaps in motifs based on experimental data. For that matter, the same fact could also explain the often underestimated preference of Met at various positions in different receptors.

A number of deviations between theoretical and experimental data exist. The tiny side-chains Ala and Gly are underpredicted at P2 by about 1 order of magnitude in Kd. This is often seen at other positions as well. A possible explanation could be the presence of structured water molecules which are ignored in the simulations. The underpredicted Gln might be explained in the same way. Structural analysis showed that Gln at P2 adopts an identical conformation as in A2, but its van der Waals interactions are reduced by ~1 kcal/mol (equivalent to ~2.5 kJ/mol), due to the mutation Phe→Ser at receptor position A9. Given the constitution of the pocket, it is likely that one or more water molecules further stabilize the free $O_\in$ atom of Gln. After all, Gln is a well accepted (and commonly underestimated) residue at P2 in A24.

Position P9 in A24 is a difficult case. The pocket at P9 is very large but not well shaped to accommodate bulky side-chains. Only Trp can take full advantage of the Leu→Ala mutation at A81 but even here it suffers from a significant compensatory strain (ranging from 4.6 to 8.5 kcal/mol in the three models). Phe experiences less strain but the latter is also strongly fluctuating (0.7 to 5.5 kcal/mol). All in all, both Trp and Phe receive similar scores, in agreement with experiment, but both are somewhat underestimated presumably due to incomplete relaxation in the simulations.

The P9 position in A24 is also special for another reason, namely its enormous diversity in binding affinity. The experimental affinity range spans 27 kJ/mol or ~5 orders of magnitude in Kd. As much as 10 of the 20 residue types (50%) cause very poor binding. The reason for this pronounced specificity is related to the weird shape of the F-pocket. Side-chains larger than Ala tend to bump into the relatively rigid wall formed by A77-Asn, A116-Tyr and A147-Trp. This causes a residual strain of 1 kcal/mol (~2.5 kJ/mol) or higher. More important, however, is the loss of interaction with residue A81 (Ala i.s.o. Leu) for all side-chains that do not properly fill the pocket. Finally, the Ala mutation leaves a fully hydrophobic hole that does not harbor structured water well. The combination of these three effects ensures that small and/or polar side-chains are absolutely unwanted at P9 in A24. Though conceptually understood, the peculiarities of the P9 region severely complicate modeling, which explains why the predicted values fluctuate more than they usually do. Nevertheless, the global standard error remains acceptable (5.0 kJ/mol) and the top-5 predicted residues (Trp, Phe, Ile, Met and Leu) exactly coincide with the experimental top-5.

When pooled, the predicted affinities of all peptides tested on A2 and A24 correlate with an $R^2$ of 0.77 and a standard error of 3.85 kJ/mol (0.67 logKd). The only true outlier is His at A24-P9. Note that no experimental information (apart from the calibration needed for conversion to free energy units) was used in the development of this purely structure-based scoring method. The method is therefore totally unbiased, the advantages of which show up in the discovery of previously unknown anchor preferences.

Example 5

Binding Specificity of B7

The inventors wanted to examine the performance of PepScope on HLA-B*0702 (B7), a receptor with a pronounced preference for Pro at position P2 and a P9 specificity with shared features from A2 and A24. Especially the P2 profile seemed intriguing: according to a point mutation analysis by Sidney et al. on the HIV nef 84-92 peptide (FPVRPQVPL), all P2 mutants were binding at least 100 times weaker than the native peptide sequence, thus only the wt Pro would be allowed at P2.

The inventors followed exactly the same approach as for A2 in the scoring of all possible amino acid side-chains at positions P2 and P9 in three B7 models. Table II shows the averaged total scores for the side-chains in a pA1a/B7 context. These values were compared to those of Sidney et al and two frequently used scoring matrices, i.e. Bimas and Syfpeithi.

TABLE II

| HLA-B7 Anchor Specificity | | | | | | | | | |
|---|---|---|---|---|---|---|---|---|---|
| | P2 | | | | | P9 | | | |
| AA | PepScope score (kcal/mol) | Sidney Kd (nM) | Bimas score (a.u.) | Syfpeithi score (a.u.) | AA | PepScope score (kcal/mol) | Sidney Kd (nM) | Bimas score (a.u.) | Syfpeithi score (a.u.) |
| P | −4.8 | 13 | 20 | 10 | M | −3.5 | 3.8 | 10 | 6 |
| A | −1.9 | >1300 | 3 | 0 | L | −2.3 | 13.6 | 40 | 10 |
| S | −0.9 | >1300 | 1 | 0 | I | −1.8 | 22.4 | 4 | 6 |
| C | −0.6 | ND | 1 | 0 | F | −1.7 | 9.5 | 0.2 | 6 |
| V | −0.5 | ND | 5 | 0 | V | −1.1 | 23.8 | 2 | 6 |
| T | −0.5 | >1300 | 1 | 0 | A | −0.7 | 62.3 | 1 | 6 |
| G | 0.0 | >1300 | 1 | 0 | H | −0.3 | 238 | 0.1 | 0 |

TABLE II-continued

HLA-B7 Anchor Specificity

| | P2 | | | | | P9 | | | |
|---|---|---|---|---|---|---|---|---|---|
| AA | PepScope score (kcal/mol) | Sidney Kd (nM) | Bimas score (a.u.) | Syfpeithi score (a.u.) | AA | PepScope score (kcal/mol) | Sidney Kd (nM) | Bimas score (a.u.) | Syfpeithi score (a.u.) |
| M | 0.7 | ND | 1 | 0 | G | 0.0 | ND | 0.1 | 0 |
| N | 0.8 | >1300 | 1 | 0 | W | 0.0 | 345 | 0.2 | 0 |
| I | 1.2 | ND | 1 | 0 | K | 0.4 | >380 | 0.1 | 0 |
| L | 1.2 | >1300 | 1 | 0 | Y | 0.6 | >380 | 0.2 | 0 |
| E | 1.5 | ND | 0.1 | 0 | R | 0.7 | ND | 0.1 | 0 |
| H | 1.7 | ND | 0.1 | 0 | S | 0.9 | ND | 0.2 | 0 |
| D | 2.0 | >1300 | 0.1 | 0 | T | 1.0 | >380 | 1 | 6 |
| Q | 2.0 | >1300 | 1 | 0 | Q | 1.0 | >380 | 0.1 | 0 |
| W | 2.1 | ND | 0.1 | 0 | C | 1.2 | >380 | 1 | 0 |
| Y | 2.5 | ND | 0.1 | 0 | D | 1.3 | >380 | 0.1 | 0 |
| F | 3.0 | >1300 | 0.1 | 0 | P | 1.4 | ND | 0.1 | 0 |
| R | 3.0 | ND | 0.1 | 0 | E | 2.8 | ND | 0.1 | 0 |
| K | 3.0 | >1300 | 0.1 | 0 | N | 3.0 | >380 | 0.2 | 0 |

AA, amino acid placed at the indicated anchor position (P2/P9) of the peptide FPVRPQVPL in the B7 complex;
PepScope score, uncalibrated affinity score;
Sidney Kd, dissociation constant published by Sidney et al.[55];
Bimas score (prediction score[51]);
Syfpeithi score (prediction score[54]);
a.u., arbitrary units.

PepScope indeed came up with Pro as the elected P2 residue. The gap with the second best (Ala) was about 3 kcal/mol, which is one of the largest differences the inventors ever observed. Yet, if the Sidney profile based on a single peptide sequence were true in general, then the Ala score would still be somewhat overestimated. Analysis of the structural data indicated that the primary reason for the observed profile is the steric repulsion of all side-chains larger than Gly, Ala, Pro and Ser. The Pro ring hydrocarbons fill the pocket in a strainless fashion and make strong van der Waals interactions (−8.1 kcal/mol), so it only has to compensate for desolvation. Ala can also bind free of strain but interacts more weakly (−3.6 kcal/mol). Val makes identical van der Waals interactions as Pro (−8.2 kcal/mol) but induces 4.4 kcal/mol of strain; together with the desolvation term (3.7 kcal/mol) and the minor electrostatics (−0.3 kcal/mol), the balance becomes slightly favorable (−0.5 kcal/mol). Unfortunately, Sidney et al. do not provide data for the Val mutant but the Bimas matrix takes it up as a feasible residue. Several other side-chains can make relatively strong interactions but they invariably pay a very high "strain" price for it (e.g. Leu). Ser, Thr and Asn are subject to a more delicate balance between different energetic contributions: in the three models they make 1-2 (Ser and Thr) or 2-3 (Asn) H-bonds, but again this is overcompensated by induced strain. If the latter were not the case, these residue types would have even been preferred. The question may be asked whether the computed strain terms for these small residues are real, but the experimental data force to conclude affirmative.

Position P9 has totally different features. Its profile looks similar to that of A2-P9 and A24-P9, with a strong preference for Met, Leu, Ile, Val and Phe. The relatively strong affinity for Phe (and even Trp), in spite of the absence of the receptor A81 Leu→Ala mutation, could be explained by a tendency of the F-pocket to open up as a result of Asp A114 attracting Tyr A116 by means of a H-bond. Another striking observation is that the top-ranked residue type, Met, is indeed identified by Sidney et al as the most potent one. Note that neither Bimas nor Syfpeithi have correctly appraised the capacity of Met. Also, Phe is significantly misjudged by Bimas: the coefficient <1 in the scoring table suggests it is disfavored while it is actually one of the best. Overall, it can be concluded that the scores of the present invention are in much better agreement with experimental affinities than the ranking by both Bimas and Syfpeithi.

Example 6

Binding Specificity of A1

Having examined the anchor specificity of two typically hydrophobic (A2 and A24) and one sterically driven receptor (B7), the inventors decided to test PepScope on a more polar system. HLA-A*0101 (A1) is such a receptor, showing marked preference for Asp and Glu at P3 (not P2) and Tyr, Lys, Arg and Phe, at P9. Position P2 prefers small, polar side-chains like Thr and Ser but a pronounced motif has not been identified. Hydrophobic side-chains seem to play an inferior role in general. The A1 system was therefore considered as an important test case for the validation of the solvent model and the scoring of H-bonds and electrostatic interactions.

Since no studies on systematic anchor substitutions are available, the scores of this invention were compared with Bimas data (FIG. 3). The first impression is that the results from both methods are in fair agreement. There is a consensus about strong binding capacity of Thr at P2, Asp and Glu at P3 and Tyr, Lys, Phe and Arg at P9. Both methods also agree about the prohibitive nature of Glu, His, Phe, Arg, Trp and Lys at P2, Arg and Lys at P3 and Pro, Asp and Glu at P9. However, some deviations are observed as well. According to the computations, Tyr is a poor yet tolerated residue at P2, while Bimas considers it to be prohibitive. The peptide IYQYMD-DLY has been identified as a medium-affinity binder, suggesting that Tyr at P2 is at least feasible. Met and Trp at P3 and P9 are ranked higher by PepScope than by Bimas. The latter is recurrently observed for most receptor systems, and is supported by direct affinity measurements. Finally, Thr received the fourth best score at P9 (−2.7 kcal/mol), similar to the known anchors Phe and Arg, while Bimas assigns a neutral score (1.0). The inventors know of only one experimental example with Thr at P9, but it is quite convincing: the strongest A1-binding peptide from HPV-18 was found to be YSDSVYGDT, with a Kd of 188 nM.

The underlying structural reasons for the observed polar preferences were examined A common feature for Thr/Ser at P2, Asp/Glu at P3 and Lys/Arg at P9 is their ability to bind relatively free of strain (the highest tensions were ~1.5 kcal/mol for Asp/Glu at P3 and 2.5 kcal/mol for Arg at P9). Thus, the interactions made by these residues in the complex are compensated only for desolvation energy (FIG. 1). The OH-functions of both Ser and Thr at P2 can form two nearly ideal H-bonds (one as donor to Glu-A63 and one as acceptor from Asn-A66) for which they receive −2.4 kcal/mol. They also receive an equal (Ser) or slightly better (Thr: −2.9 kcal/mol) amount of electrostatic energy. Together with the other interactions, the balance is slightly in favor of Thr (−2.6 kcal/mol), immediately followed by Ser (−2.0 kcal/mol). The total scores for Ser and Thr are "good" though not "excellent"; another H-bond would be needed to make them elected anchors.

Asp and Glu, in contrast, are true anchor residues at position P3. Asp can form a double bifurcated H-bond with Arg-A156 (−3.1 kcal/mol) and receives an extra −6.2 kcal/mol electrostatic energy, mainly from the same Arg but also from the peptide backbone NH dipoles of residues P3 and P5. Glu forms two suboptimal H-bonds with Arg-A156 and another weak H-bond with His-A70, for which it receives a total of −2.7 and −5.2 kcal/mol in H-bonding and electrostatic energy, respectively.

Lys and Arg at P9 can both form a single H-bond with Asp-A116 (yielding −1.4 and −1.9 kcal/mol, respectively), but the electrostatics are only of moderate quality (−1.2 and −1.8 kcal/mol, respectively). However, Lys can bind in a totally relaxed way, while Arg induces 2.5 kcal/mol of strain. The van der Waals interactions largely suffice to compensate for desolvation, so that the end balance for both is relatively favorable (−4.2 and −2.6 kcal/mol, respectively). For comparison, Tyr has a total energy of −5.7 kcal/mol, a value that can rightly be associated with a strong anchor.

REFERENCES

1. Rosenfeld R, Zheng Q, Vajda S, DeLisi C. Flexible docking of peptides to class I major-histocompatibility-complex receptors. Genet Anal 1995; 12:1-21.
2. Desmet J, Wilson I A, Joniau M, De Maeyer M, Lasters I. Computation of the binding of fully flexible peptides to proteins with flexible side chains. FASEB J 1997; 11:164-172.
3. Dunbrack R L, Karplus M. Conformational analysis of the backbone-dependent rotamer preferences of protein sidechains. Nature Struct Biol 1994; 1:335-340.
4. De Maeyer M, Desmet J, Lasters I. All in one: a highly detailed rotamer library improves both accuracy and speed in the modelling of sidechains by dead-end elimination. Fold Des 1997; 2:53-66.
5. Schrauber H, Eisenhaber F, Argos P. Rotamers: to be or not to be? An analysis of amino acid side-chain conformations in globular proteins. J Mol Biol 1993; 230:592-612.
6. Mendes J, Baptista A M, Carrondo M A, Soares C M. Improved modeling of side-chains in proteins with rotamer-based methods: a flexible rotamer model. Proteins 1999; 37:530-543.
7. Madden D R, Garboczi D N, Wiley D C. The antigenic identity of peptide-MHC complexes: a comparison of the conformations of five viral peptides presented by HLA-A2. Cell 1993; 75:693-708.
8. Chen Y, Sidney J, Southwood S, Cox A L, Sakaguchi K, Henderson R A, Appella E, Hunt D F, Sette A, Engelhard V H. Naturally processed peptides longer than nine amino acid residues bind to the class I MHC molecule HLA-A2.1 with high affinity and in different conformations. J Immunol 1994; 152:2874-2881.
9. Batalia M A, Collins E J. Peptide binding by class I and class II MHC molecules. Biopolymers 1997; 43:281-302.
10. Persson K, Schneider G. Three-dimensional structures of MHC class I-peptide complexes: implications for peptide recognition. Arch Immunol Ther Exp 2000; 48:135-142.
11. Guo H C, Jardetzky T S, Garrett T P, Lane W S, Strominger J L, Wiley D C. Different length peptides bind to HLA-Aw68 similarly at their ends but bulge out in the middle. Nature 1992; 360:364-366.
12. Stern L J, Wiley D C. Antigenic peptide binding by class I and class II histocompatibility proteins. Structure 1994; 2:245-251.
13. Zhang W, Young A C M, Imarai M, Nathenson S G, Sacchettini J C. Crystal structure of the major histocompatibility complex class I H-2K$^b$ molecule containing a single viral peptide: implications for peptide binding and T-cell receptor recognition. Proc Natl Acad Sci USA 1992; 89: 8403-8407.
14. Smith K J, Reid S W, Harlos K, McMichael A J, Stuart D I, Bell J I, Jones E Y. Bound water structure and polymorphic amino acids act together to allow the binding of different peptides to MHC class I HLA-B53. Immunity 1996; 4:215-228.
15. Levy Y, Onuchic J N. Water and proteins: a love-hate relationship. Proc Natl Acad Sci USA 2004; 101:3325-3326.
16. Gilis D, Rooman M. Stability changes upon mutation of solvent-accessible residues in proteins evaluated by database-derived potentials. J Mol Biol 1996; 257:1112-1126.
17. Sippl M J, Ortner M, Jaritz M, Lackner P, Flockner H. Helmholtz free energies of atom pair interactions in proteins. Fold Des 1996; 1:289-298.
18. Jernigan R L, Bahar I. Structure-derived potentials and protein simulations. Curr Opin Struct Biol 1996; 6:195-209.
19. Böhm H J. The development of a simple empirical scoring function to estimate the binding constant for a protein-ligand complex of known three-dimensional structure. J Comput Aid Mol Des 1994; 8:243-256.
20. Weng Z, Vajda S, DeLisi C. Prediction of complexes using empirical free energy functions. Protein Sci 1996; 5:614-626.
21. Vajda S, Sippl M, Novotny J. Empirical potentials and functions for protein folding and binding. Curr Opin Struct Biol 1997; 7:222-228.
22. Wang R, Lai L, Wang S. Further development and validation of empirical scoring functions for structure-based binding affinity prediction. J Comput Aid Mol Des 2002; 16:11-26.
23. Doytchinova I A, Flower D R. Physicochemical explanation of peptide binding to HLA-A*0201 major histocompatibility complex: a three-dimensional quantitative structure-activity relationship study. Proteins 2002; 48:505-518.
24. Guerois R, Nielsen J E, Serrano L. Predicting changes in the stability of proteins and protein complexes: a study of more than 1000 mutations. J Mol Biol 2002; 320:369-387.
25. Froloff N, Windemuth A, Honig B. On the calculation of binding free energies using continuum methods: application to MHC class I protein-peptide interactions. Protein Sci. 1997; 6:1293-1301.

26. Rognan D, Lauemøller S L, Holm A, Buus S, Tschinke V. Predicting binding affinities of protein ligands from three-dimensional models: application to peptide binding to class I major histocompatibility proteins. J Med Chem 1999; 42:4650-4658.
27. Schapira M, Totrov M, Abagyan R. Prediction of the binding energy for small molecules, peptides and proteins. J Mol Recognit 1999; 12:177-190.
28. Engelhard V H. Structure of peptides associated with MHC class I molecules. Curr Opin Immunol 1994; 6:13-23.
29. Bjorkman P J, Saper M A, Samraoui B, Bennett W S, Strominger J L, Wiley D C. The foreign antigen binding site and T cell recognition regions of class I histocompatibility antigens. Nature 1987; 329:512-528.
30. Berman H M, Westbrook J, Feng Z, Gilliland G, Bhat T N, Weissig H, Shindyalov I N, Bourne P E. The Protein Data Bank. Nucleic Acids Res 2000; 28:235-242.
31. Saper M A, Bjorkman P J, Wiley D C. Refined structure of the human histocompatibility antigen HLA-A2 at 2.6 Å. J Mol Biol 1991; 219:277-319.
32. Ruppert J, Sidney J, Celis E, Kubo R T, Grey H M, Sette A. Prominent role of secondary anchor residues in peptide binding to HLA-A2.1 molecules. Cell 1993; 74:929-937.
33. Matsumura M, Fremont D H, Peterson P A, Wilson I A. Emerging principles for the recognition of peptide antigens by MHC class I molecules. Science 1992; 257:927-934.
34. Ogata K, Jaramillo A, Cohen W, Briand J P, Connan F, Choppin J, Muller S, Wodak S J. Automatic sequence design of major histocompatibility complex class I binding peptides impairing CD8$^+$ T cell recognition. J Biol Chem 2003; 278:1281-1290.
35. Gordon D B, Marshall S A, Mayo S L. Energy functions for protein design. Curr Opin Struct Biol 1999; 9:509-513.
36. Brooks B R, Bruccoleri R E, Olafson B D, States D J, Swaminathan S, Karplus M. CHARMM: a program for macromolecular energy minimization and dynamics calculations. J Comput Chem 1983; 4:187-217.
37. Wolfenden R, Andersson L, Cullis P M, Southgate C C. Affinities of amino acid side chains for solvent water. Biochemistry 1981; 20:849-855.
38. Ooi T, Oobatake M, Nemethy G, Scheraga H A. Accessible surface areas as a measure of the thermodynamic parameters of hydration of peptides. Proc Natl Acad Sci USA 1987; 84:3086-3090.
39. Wimley W C, Creamer T P, White S H. Solvation energies of amino acid side chains and backbone in a family of host-guest pentapeptides. Biochemistry 1996; 35:5109-5124.
40. Desmet J, Spriet J, Lasters I. Fast and accurate side-chain topology and energy refinement (FASTER) as a new method for protein structure optimization. Proteins 2002; 48:31-43.
41. Desmet J, De Maeyer M, Spriet J, Lasters I. Flexible docking of peptide ligands to proteins. In: Webster D, ed. Methods in Molecular Biology, vol. 143: Protein Structure Prediction: Methods and Protocols. Totowa, N.J.: Humana Press 2000. p 359-376.
42. Eisenberg D, McLachlan A D. Solvation energy in protein folding and binding. Nature 1986; 319:199-203.
43. Lazaridis T, Karplus M. Effective energy function for proteins in solution. Proteins 1999; 35:133-152.
44. Warshel A, Levitt M. Theoretical studies of enzymatic reactions: dielectric, electrostatic and steric stabilization of the carbonium ion in the reaction of lysozyme. J Mol Biol 1976; 103:227-249.
45. Jorgensen W L, Chandrasekhar J, Madura J D, Impey R W, Klein M L. Comparison of simple potential functions for simulating liquid water. J Chem Phys 1983; 79:926-935.
46. van der Burg S H, Ras E, Drijfhout J W, Benckhuijsen W E, Bremers A J, Melief C J M, Kast W M. An HLA class I peptide-binding assay based on competition for binding to class I molecules on intact human B cells. Identification of conserved HIV-1 polymerase peptides binding to HLAA*0301. Hum Immunol 1995; 44:189-98.
47. Kessler J H, Mommaas B, Mutis T, Huijbers I, Vissers D, Benckhuijsen W E, Schreuder G M, Offring a R, Goulmy E, Melief C J, van der Burg S H, Drijfhout J W. Competition-based cellular peptide binding assays for 13 prevalent HLA class I alleles using fluorescein-labeled synthetic peptides. Hum Immunol 2003; 64:245-55.
48. Falk K, Rötzschke O, Stevanovic S, Jung G, Rammensee H G. Allele specific motifs revealed by sequencing of self-peptides eluted from MHC molecules. Nature 1991; 351: 290-296.
49. Rötzschke O, Falk K, Stevanovic S, Jung G, Rammensee H G. Peptide motifs of closely related HLA class I molecules encompass substantial differences. Eur J Immunol 1992; 22:2453-2456.
50. Marsh S G E, Parham P, Barber L D. The HLA FactsBook. San Diego: Academic Press 2000.
51. Parker K C, Bednarek M A, Coligan J E. Scheme for ranking potential HLA-A2 binding peptides based on independent binding of individual peptide side-chains. J Immunol 1994; 152:163-175.
52. Parker K C, Shields M, DiBrino M, Brooks A, Coligan J E. Peptide binding to MHC class I molecules: implications for antigenic peptide prediction Immunol Res 1995; 14:34-57.
53. Rudolf M P, Man S, Melief C J M, Sette A, Kast W M. Human T-cell responses to HLA-A-restricted high binding affinity peptides of human papillomavirus type 18 proteins E6 and E7. Clin Cancer Res 2001; 7(3Suppl):788s-795s.
54. Rammensee H-G, Bachmann J, Emmerich N P, Bachor O A, Stevanovic S. SYFPEITHI: database for MHC ligands and peptide motifs Immunogenetics 1999; 50:213-219.
55. Sidney J, Southwood S, del Guercio M F, Grey H M, Chesnut R W, Kubo R T, Sette A. Specificity and degeneracy in peptide binding to HLA-B7-like class I molecules. J Immunol 1996; 157:3480-3490.
56. Sette A, Kubo R T, Sidney J, Celis E, Grey H M, Southwood S. HLA-binding peptides and their uses. 1999; WO 99/45954.
57. Stern H A, Kaminski G A, Banks J L, Zhou R, Berne B J, Friesner R A. Fluctuating charge, polarizable dipole, and combined models: parameterization from ab initio quantum chemistry. J Phys Chem B 1999; 103:4730-4737.
58. Doytchinova I A, Blythe M J, Flower D R. Additive method for the prediction of protein-peptide binding affinity. Application to the MHC class I molecule HLA-A*0201. J Proteome Res 2002; 1:263-272.
59. Peters B, Tong W, Sidney J, Sette A, Weng Z. Examining the independent binding assumption for binding of peptide epitopes to MHC-I molecules. Bioinformatics 2003; 19:1765-1772.

The invention claimed is:

1. A method for determining an affinity score for a protein/ligand complex useful for estimating the affinity of the ligand for the protein, wherein said score is solely based on structural data and a force field function, the method comprising:
   (a) estimating desolvation energy for the ligand by a method comprising in silico simulation of immersion of one or more individual amino acid side-chains of the ligand; wherein the side-chains include at least one anchor residue, and are present in the ligand as amino acid model compounds in a solvent box filled with explicit water molecules, and applying the force field function to estimate the desolvation energy;

(b) calculating ligand/protein complex interaction energy by a method comprising modeling with a computer a structural representation of the ligand placed in a binding site of the protein and applying the same force field function as used to estimate the desolvation energy in order to calculate the ligand/protein interaction energy;

(c) calculating a conformational strain energy for the protein/ligand representation of step (b) by a method comprising applying the same force field function; and (d) subtracting the desolvation energy of step (a) and the conformational strain energy of step (c) from the ligand/protein interaction energy of step (b) to obtain said affinity score.

2. The method of claim 1 wherein the conformational strain energy of step (c) is calculated as the difference between the sum of conformational energies of the ligand and protein in an unbound reference state and the sum of the conformational energies of the ligand and the protein in the protein/ligand representation of step (b).

3. The method of claim 1, wherein the protein/ligand representation of step (b) is derived from an experimentally determined structure.

4. The method of claim 1, wherein the modeling by the computer in step (b) comprises an energy minimization step.

5. The method of claim 1, wherein the representation of the protein in step (b) is derived from an experimentally determined structure.

6. The method of claim 1, wherein the protein to which the ligand binds is a receptor.

7. The method of claim 1, wherein the ligand is a peptide, a small molecule or a pharmacophore.

8. The method of claim 1, wherein calculating the affinity score further comprises determining the affinity score for one or more additional anchor residues in the protein/ligand complex.

9. The method of claim 8, wherein the protein-ligand complex comprises a MHC receptor/ligand complex.

10. A method for determining an affinity score of an anchor residues in a protein/ligand complex, wherein said score is solely based on structural data and a force field, this method comprising (a) estimating desolvation energy for the anchor residue by a method comprising in silico simulation of individual amino acid model compounds in a solvent box filled with explicit water molecules, and applying the force field function to estimate the desolvation energy for the anchor residue;

(b) calculating by a ligand-protein interaction energy at the anchor residue positions by a method comprising modeling with a computer a structural representation of the ligand placed in the binding site of the protein and applying the force field function to calculate the ligand-protein interaction energy for the anchor residue;

(c) calculating by modeling with a computer a conformational strain energy at the anchor residue positions for the protein/ligand representation of step (b) and applying the force field function to calculate the conformational strain energy at the anchor residue position; and (d) calculating said affinity score for the anchor residues by subtracting the desolvation energy of step (a) and the conformational strain energy of step (c) from the ligand-protein interaction energy of step (b).

11. The method of claim 10, wherein the conformational strain energy of step (c) is calculated as the difference between the sum of conformational energies of the ligand and protein in an unbound reference state and the sum of the conformational energies of the ligand and the protein in the protein/ligand representation of step (b).

12. The method of claim 6, wherein the receptor is a MHC receptor.

13. The method of claim 8, wherein the affinity score of each anchor residue is calculated by computer modeling that includes amino acid side-chain rotameric analysis.

14. The method of claim 13, wherein the computer modeling comprises individually substituting the amino acid side-chain at each anchor residue to form a rotameric variant and computing a total energy score for the rotameric variant 15. The method of claim 14, wherein the total energy score is computed according to the following formula:

$$E_{total} = \min_r \{E_{desolv}(r) + E_{inter}(r) + E_{strain}(r)\};$$

wherein r is the rotameric variant, $E_{desolv}$ is desolvation energy, $E_{inter}$ is side-chain/receptor non-bonded interactions, and $E_{strain}$ is conformational strain energy.

16. The method of claim 15, wherein $E_{desolv}$ is $-\Sigma_i \% BSA(i) \times GSP(i)$ and % BSA is percentage buried surface area, GSP is group solvation parameters, and i is a function of the substituted amino acid side-chain selected from aliphatic $C_xH_y$, aromatic $C_xH_y$, aromatic $N_xH_y$, hydroxyl, sulphur, sulphydryl, charged amine, carboxyl, amide, or guanidinium.

17. The method of claim 15, wherein $E_{inter}$ is $\Sigma\{E_{vdw}(i) + E_{hbo}(i) + E_{ele}(i)\}$ and $E_{vdw}$ is Van der Waals interactions, $E_{hbo}$ is H-bond interactions, $E_{ele}$ is electrostatic interactions, and i is a function of the substituted amino acid side-chain selected from aliphatic $C_xH_y$, aromatic $C_xH_y$, aromatic $N_xH_y$, hydroxyl, sulphur, sulphydryl, charged amine, carboxyl, amide, or guanidinium.

18. The method of claim 15, wherein $E_{strain}$ is $E_{rec} + E_{pep} + E_{self}$ and $E_{rec}$, is strain energy in the receptor, $E_{pep}$ is strain of the peptide minus strain of the substituted amino acid side-chain, and $E_{self}$ is self-tension of the substituted amino acid side-chain.

19. The method of claim 10, wherein step (a) further comprises calculating the % buried surface area (% BSA) for the anchor residue by a method comprising modeling with a computer a structural representation of the ligand placed in the binding site of the protein.

20. The method of claim 1, for determining an affinity score for a protein/ligand complex useful for estimating the affinity of the ligand for the protein, wherein said score is solely based on structural data and a force field function, wherein the force field function is a CHARMM force field.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: HBV POL 676-684 peptide

<400> SEQUENCE: 1

Phe Leu Ser Lys Gln Tyr Met Thr Leu
1               5

<210> SEQ ID NO 2
<211> LENGTH: 9
<212> TYPE: PRT
<213> ORGANISM: Artificial Sequence
<220> FEATURE:
<223> OTHER INFORMATION: HBV POL 676-684 derived peptide, with 39 anchor
      substitutions at positions P2 and P9
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Phe Xaa Ser Lys Gln Tyr Met Thr Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: High affinity peptide for A1

<400> SEQUENCE: 3

Tyr Thr Ala Val Val Pro Leu Val Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: HIV nef 84-92 peptide

<400> SEQUENCE: 4

Phe Pro Val Arg Pro Gln Val Pro Leu
1               5

<210> SEQ ID NO 5
<211> LENGTH: 10
<212> TYPE: PRT
<213> ORGANISM: Artificial Sequence
<220> FEATURE:
<223> OTHER INFORMATION: Fluorescent reference peptide for A2
<220> FEATURE:
<221> NAME/KEY: misc_feature
<222> LOCATION: (6)..(6)
<223> OTHER INFORMATION: Fluorescein labeled Cys

<400> SEQUENCE: 5

Phe Leu Pro Ser Asp Xaa Phe Pro Ser Val
```

```
<210> SEQ ID NO 6
<211> LENGTH: 9
<212> TYPE: PRT
<213> ORGANISM: Artificial Sequence
<220> FEATURE:
<223> OTHER INFORMATION: Fluorescent reference peptide for A24
<220> FEATURE:
<221> NAME/KEY: misc_feature
<222> LOCATION: (5)..(5)
<223> OTHER INFORMATION: Fluorescein labeled Cys

<400> SEQUENCE: 6

Arg Tyr Leu Lys Xaa Gln Gln Leu Leu
1               5

<210> SEQ ID NO 7
<211> LENGTH: 9
<212> TYPE: PRT
<213> ORGANISM: Artificial Sequence
<220> FEATURE:
<223> OTHER INFORMATION: HBV POL 676-684 derived peptide

<400> SEQUENCE: 7

Phe Cys Ser Lys Gln Tyr Met Thr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: HBV POL 676-684 derived peptide

<400> SEQUENCE: 8

Phe Leu Ser Lys Gln Tyr Met Thr Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Medium-affinity binder for A1 (Example 6)

<400> SEQUENCE: 9

Ile Tyr Gln Tyr Met Asp Asp Leu Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Strongest A1-binding peptide from HPV-18

<400> SEQUENCE: 10

Tyr Ser Asp Ser Val Tyr Gly Asp Thr
1               5
```